(12) United States Patent
Mammen et al.

(10) Patent No.: US 7,250,414 B2
(45) Date of Patent: Jul. 31, 2007

(54) DIPHENYLMETHYL COMPOUNDS USEFUL AS MUSCARINIC RECEPTOR ANTAGONISTS

(75) Inventors: Mathai Mammen, Redwood Shores, CA (US); Yu-Hua Ji, Redwood City, CA (US); Yan Chen, Burlingame, CA (US); Craig Husfeld, Redwood City, CA (US)

(73) Assignee: Theravance, Inc., South San Francisco, CA (US)

( * ) Notice: Subject to any disclaimer, the term of this patent is extended or adjusted under 35 U.S.C. 154(b) by 131 days.

(21) Appl. No.: 11/077,391

(22) Filed: Mar. 10, 2005

(65) Prior Publication Data

US 2005/0203167 A1 Sep. 15, 2005

Related U.S. Application Data

(60) Provisional application No. 60/552,401, filed on Mar. 11, 2004.

(51) Int. Cl.
C07D 207/08 (2006.01)
C07D 413/14 (2006.01)
C07D 403/14 (2006.01)
A61K 31/4025 (2006.01)
A61K 31/5377 (2006.01)

(52) U.S. Cl. .............. 514/235.5; 514/254.01; 514/255.05; 514/422; 544/141; 544/336; 544/372; 548/517; 548/527; 548/568

(58) Field of Classification Search ............. 548/567
See application file for complete search history.

(56) References Cited

U.S. PATENT DOCUMENTS

| | | | |
|---|---|---|---|
| 3,192,221 A | 6/1965 | Lunsford et al. | |
| 3,247,222 A | 4/1966 | Lunsford | |
| 3,732,247 A | 5/1973 | Helsley et al. | |
| 3,984,557 A | 10/1976 | Welstead, Jr. | |
| 4,002,766 A | 1/1977 | Welstead, Jr. | |
| 4,594,343 A | 6/1986 | Shanklin, Jr. | |
| 4,810,713 A | 3/1989 | Yanni et al. | |
| 4,950,674 A | 8/1990 | Yanni et al. | |
| 5,070,087 A | 12/1991 | Teng et al. | |
| 5,096,890 A | 3/1992 | Cross et al. | |
| 5,340,831 A | 8/1994 | Cross et al. | |
| 5,344,835 A | 9/1994 | Alker et al. | |
| 5,486,527 A | 1/1996 | Alker et al. | |
| 5,607,950 A | 3/1997 | Alker et al. | |
| 5,750,540 A | 5/1998 | Tsuchiya et al. | |
| 5,932,594 A | 8/1999 | Cross et al. | |
| 6,130,232 A | 10/2000 | Mase et al. | |
| 6,403,810 B2 * | 6/2002 | Klaus et al. | 549/71 |
| 6,433,027 B1 | 8/2002 | Bozung et al. | |
| 6,693,202 B1 | 2/2004 | Aggen et al. | |
| 2003/0018019 A1 | 1/2003 | Meade et al. | |
| 2004/0122014 A1 | 6/2004 | Mammen et al. | |
| 2004/0254219 A1 | 12/2004 | Mammen et al. | |
| 2005/0026954 A1 | 2/2005 | Mammen et al. | |

FOREIGN PATENT DOCUMENTS

| | | |
|---|---|---|
| EP | 0 178 946 A2 | 4/1986 |
| EP | 0 235 463 A2 | 9/1987 |
| EP | 0 999 205 A1 | 5/2000 |
| EP | 1 020 449 A1 | 7/2000 |
| JP | 11 100366 | 4/1999 |
| WO | WO 95/06635 A1 | 3/1995 |
| WO | WO 98/54167 A1 | 12/1998 |
| WO | WO 2004/089892 A2 | 10/2004 |

OTHER PUBLICATIONS

Yeh et al., "Molecular and Structural Basis of Resting and Use-dependent Block of Sodium Current Defined Using Disopyramide Analogues," Biophysical Journal, vol. 51, p. 123-135 (1987).*
U.S. Appl. No. 10/813,745, filed Mar. 31, 2004, Mammen et al.
U.S. Appl. No. 10/975,657, filed Oct. 28, 2004, Wilson et al.
U.S. Appl. No. 11/076,658, filed Mar. 10, 2005, Mammen et al.
Broadley et al., "Muscarinic Receptor Agonists and Antagonists", Molecules, 6, pp. 142-193 (2001).
Cale et al., "A Series of Central Nervous System Stimulants Based on the 4-Substituted 3,3-Diphenyl-2-pyrrolidinone Skeleton. II", J. Med. Chem., 10(2), pp. 214-222 (1967).
Eglen et al., "Muscarinic Receptor Subtypes:Pharmacology and Therapeutic Potential", DN&P, 10(8), pp. 462-469 (1997).

(Continued)

Primary Examiner—Golam M. M. Shameem
Assistant Examiner—Andrew B. Freistein
(74) Attorney, Agent, or Firm—Jeffrey A. Hagenah; Shelley Eberle

(57) ABSTRACT

This invention provides compounds of formula I:

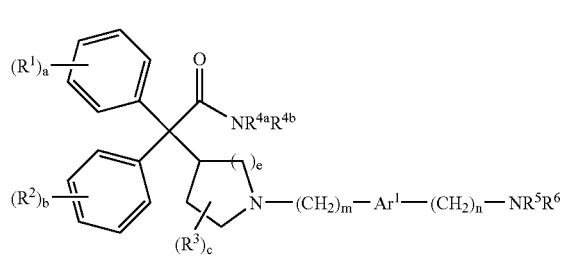

wherein a, b, c, e, m, n, $Ar^1$, $R^1$, $R^2$, $R^3$, $R^{4a}$, $R^{4b}$, $R^5$ and $R^6$ are as defined in the specification. The compounds of formula I are muscarinic receptor antagonists. The invention also provides pharmaceutical compositions containing such compounds, processes and intermediates for preparing such compounds and methods of using such compounds to treat pulmonary disorders.

25 Claims, No Drawings

OTHER PUBLICATIONS

Graul et al., "Darifenacin", Drugs of the Future, 21(11), pp. 1105-1108 (1996).

Taniguchi et al., "Agents for the Treatment of Overactive Detrusor, VI. [1a)] Synthesis and Pharmacological Properties of Acetamide Derivatives Bearing Cyclic Amines in $N$-Substitutents", Chem. Pharm. Bull, 42(1), pp. 74-84) 1994.

Zlotos et al., "Muscarinic receptor agonists and antagonists", Exp. Opin. Ther. Patents, 9(8), pp. 1029-1053 (1999).

* cited by examiner

DIPHENYLMETHYL COMPOUNDS USEFUL AS MUSCARINIC RECEPTOR ANTAGONISTS

CROSS-REFERENCE TO RELATED APPLICATIONS

This application claims the benefit of U.S. Provisional Application No. 60/552,401, filed on Mar. 11, 2004; the entire disclosure of which is incorporated herein by reference in its entirety.

BACKGROUND OF THE INVENTION

1. Field of the Invention

The present invention relates to novel diphenylmethyl compounds having muscarinic receptor antagonist or anticholinergic activity. This invention also relates to pharmaceutical compositions comprising such diphenylmethyl compounds, processes and intermediates for preparing such diphenylmethyl compounds and methods of using such diphenylmethyl compounds to treat pulmonary disorders.

2. State of the Art

Pulmonary or respiratory disorders, such as chronic obstructive pulmonary disease (COPD) and asthma, afflict many millions of people worldwide and such disorders are a leading cause of morbidity and mortality.

Muscarinic receptor antagonists are known to provide bronchoprotective effects and therefore, such compounds are useful for treating respiratory disorders, such as COPD and asthma. When used to treat such disorders, muscarinic receptor antagonists are typically administered by inhalation. However, even when administered by inhalation, a significant amount of the muscarinic receptor antagonist is often absorbed into the systemic circulation resulting in systemic side effects, such as dry mouth, mydriasis and cardiovascular side effects.

Additionally, many inhaled muscarinic receptor antagonists have a relatively short duration of action requiring that they be administered several times per day. Such a multiple-daily dosing regime is not only inconvenient but also creates a significant risk of inadequate treatment due to patient non-compliance with the required frequent dosing schedule.

Accordingly, a need exists for new muscarinic receptor antagonists. In particular, a need exists for new muscarinic receptor antagonists that having high potency and reduced systemic side effects when administered by inhalation. Additionally, a need exists for inhaled muscarinic receptor antagonists having a long duration of action thereby allowing for once-daily or even once-weekly dosing. Such compounds are expected to be particularly effective for treating pulmonary disorders, such as COPD and asthma, while reducing or eliminating side effects, such as dry-mouth and constipation.

SUMMARY OF THE INVENTION

The present invention provides novel diphenylmethyl compounds having muscarinic receptor antagonist or anticholinergic activity. Among other properties, compounds of this invention are expected to possess high potency and reduced systemic side effects when administered by inhalation and to have a long duration of action.

Accordingly, in one of its composition aspects, this invention provides a compound of formula I:

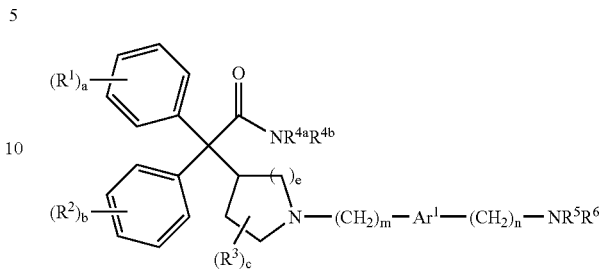

wherein
each $R^1$ and $R^2$ are independently selected from (1-4C)alkyl, (2-4C)alkenyl, (2-4C)alkynyl, (3-6C)cycloalkyl, cyano, halo, —$OR^a$, —$SR^a$, —$NR^aR^b$, —$S(O)R^c$ and —$S(O)_2R^c$; where each $R^a$ and $R^b$ independently represents hydrogen, (1-4C)alkyl, (2-4C)alkenyl, (2-4C)alkynyl or (3-6C)cycloalkyl; each $R^c$ independently represents (1-4C)alkyl, (2-4C)alkenyl, (2-4C)alkynyl or (3-6C)cycloalkyl; or two adjacent $R^1$ groups or two adjacent $R^2$ groups are joined together to form (3-6C)alkylene, (2-4C)alkylene-O— or —O-(2-4C)alkylene-O—;

a and b each independently are 0 or an integer of from 1 to 5;

each $R^3$ independently is fluoro or (1-4C)alkyl;

c is 0 or an integer of from 1 to 3;

$R^{4a}$ and $R^{4b}$ are independently selected from hydrogen, (1-4C)alkyl and phenyl-(1-4C)alkyl; or $R^{4a}$ and $R^{4b}$ together with the nitrogen atom to which they are attached form a (3-6C)heterocyclic ring optionally containing one additional heteroatom selected from nitrogen, oxygen or sulfur and wherein the heterocyclic ring is unsubstituted or substituted with 1 or 2 substituents selected independently from (1-4C) alkyl and fluoro;

e is 1 or 2;

m is 1, 2, 3 or 4;

$Ar^1$ represents a phenylene group or a (3-5C)heteroarylene group containing 1 or 2 heteroatoms selected independently from oxygen, nitrogen or sulfur; wherein the phenylene and heteroarylene groups are unsubstituted or substituted with 1 to 4 substituents selected independently from halo, (1-4C)alkyl or (1-4C)alkoxy; wherein each alkyl and alkoxy group is optionally substituted with from 1 to 3 fluoro substituents;

n is 0, 1, 2, 3 or 4;

provided that the values of m, n and $Ar^1$ are selected such that the number of contiguous atoms in the chain —$(CH_2)_m$—$Ar^1$—$(CH_2)_n$— between the two nitrogen atoms to which it is attached is in the range of from 7 to 12;

$R^5$ is selected from hydrogen, (1-6C)alkyl, $Ar^2$, —$CH_2Ar^2$ and —$CH_2CH_2NHC(O)R^{5a}$; where $Ar^2$ represents phenyl, (3-6C)cycloalkyl or (3-5C)heteroaryl containing 1 or 2 heteroatoms selected from oxygen, nitrogen or sulfur, wherein the phenyl and heteroaryl groups are unsubstituted or substituted with 1 to 3 substituents selected independently from halo, (1-4C)alkyl, (1-4C)alkoxy and methylenedioxy; and wherein $R^{5a}$ represents (1-4C)alkyl;

$R^6$ is hydrogen or (1-6C)alkyl; or $R^5$ and $R^6$ together with the nitrogen atom to which they are attached form a (3-5C) azacycloalkyl group; or when $Ar^1$ represents heteroarylene, $R^5$ and $R^6$ together with the nitrogen atom to which they are attached can additionally form a morpholin-1-yl or 4-(1-6C) alkylpiperazin-1-yl group; and wherein each alkyl group in $R^1$, $R^2$, $R^3$, $R^{4a}$, $R^{4b}$, $R^5$, $R^6$ and $R^{a-c}$ is optionally substituted with from 1 to 5 fluoro substituents;

or a pharmaceutically acceptable salt or solvate or stereoisomer thereof.

In another of its composition aspects, this invention is directed to a pharmaceutical composition comprising a pharmaceutically acceptable carrier and a therapeutically effective amount of a compound of formula I or a pharmaceutically acceptable salt or solvate or stereoisomer thereof. Such pharmaceutical compositions may optionally contain other therapeutic agents. Accordingly, in one embodiment, this invention is directed to such a pharmaceutical composition wherein the composition further comprises a therapeutically effective amount of a steroidal anti-inflammatory agent, such as a corticosteroid; a $\beta_2$ adrenergic receptor agonist; a phosphodiesterase-4 inhibitor; or a combination thereof.

Compounds of this invention possess muscarinic receptor antagonist activity. Accordingly, compounds of formula I are expected to be useful for treating pulmonary disorders, such as chronic obstructive pulmonary disease and asthma.

Accordingly, in one of its method aspects, this invention is directed to a method for treating a pulmonary disorder, the method comprising administering to a patient a therapeutically effective amount of a compound of formula I or a pharmaceutically acceptable salt or solvate or stereoisomer thereof.

Additionally, in another of its method aspects, this invention is directed to a method of producing bronchodilation in a patient, the method comprising administering to a patient a bronchodilation-producing amount of a compound of formula I or a pharmaceutically acceptable salt or solvate or stereoisomer thereof.

This invention is also directed to a method of treating chronic obstructive pulmonary disease or asthma, the method comprising administering to a patient a therapeutically effective amount of a compound of formula I or a pharmaceutically acceptable salt or solvate or stereoisomer thereof.

In another one of its method aspects, this invention is directed to a method for antagonizing a muscarinic receptor in a mammal comprising administering to the mammal, a therapeutically effective amount of the compound of formula I.

Since compounds of this invention possess muscarinic receptor antagonist activity, such compounds are also useful as research tools. Accordingly, in yet another of its method aspects, this invention is directed to a method for using a compound of formula I or a pharmaceutically acceptable salt or solvate or stereoisomer thereof as a research tool for studying a biological system or sample, or for discovering new chemical compounds having muscarinic receptor antagonist activity.

This invention is also directed to processes and novel intermediates useful for preparing compounds of formula I or a pharmaceutically acceptable salt or solvate or stereoisomer thereof. Accordingly, in another of its method aspects, this invention is directed to a process of preparing a compound of formula I, the process comprising:

(a) reacting a compound of formula II with a compound of formula III;
(b) reacting a compound of formula IV with a compound of formula V in the presence of a reducing agent;
(c) reacting a compound of formula VI with a compound of formula V;
(d) reacting a compound of formula II with a compound of formula VII in the presence of a reducing agent; or
(e) reacting a compound of formula VIII with a reducing agent;

to provide a compound of formula I; wherein compounds of formula II-VIII are as defined herein.

In one embodiment, the above process further comprises the step of forming a pharmaceutically acceptable salt of a compound of formula I. In other embodiments, this invention is directed to the other processes described herein; and to the product prepared by any of the processes described herein.

This invention is also directed to a compound of formula I or a pharmaceutically acceptable salt or solvate or stereoisomer thereof, for use in therapy or as a medicament.

Additionally, this invention is directed to the use of a compound of formula I or a pharmaceutically acceptable salt or solvate or stereoisomer thereof, for the manufacture of a medicament; especially for the manufacture of a medicament for the treatment of a pulmonary disorder or for antagonizing a muscarinic receptor in a mammal.

DETAILED DESCRIPTION OF THE INVENTION

In one of its composition aspects, this invention is directed to novel diphenylmethyl compounds of formula I or pharmaceutically acceptable salts or solvates or stereoisomers thereof. These compounds may contain one or more chiral centers and therefore, this invention is directed to racemic mixtures; pure stereoisomers (i.e., enantiomers or diastereomers); stereoisomer-enriched mixtures and the like unless otherwise indicated. When a particular stereoisomer is shown or named herein, it will be understood by those skilled in the art that minor amounts of other stereoisomers may be present in the compositions of this invention unless otherwise indicated, provided that the desired utility of the composition as a whole is not eliminated by the presence of such other isomers.

In particular, when e is 1, the compounds of formula I contain a chiral center at the carbon atom indicated by the symbol * in the following partial formula (shown without optional substituents for clarity):

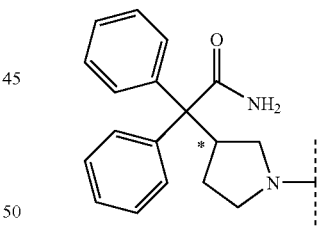

In one embodiment of this invention, the carbon atom identified by the symbol * has the (R) configuration. In this embodiment, it is preferred for compounds of formula I to have the (R) configuration at the carbon atom identified by the symbol * or to be enriched in a stereoisomeric form having the (R) configuration at this carbon atom. In another embodiment of this invention, the carbon atom identified by the symbol * has the (S) configuration. In this embodiment, it is preferred for compounds of formula I to have the (S) configuration at the carbon atom identified by the symbol * or to be enriched in a stereoisomeric form having the (S) configuration at this carbon atom.

The compounds of formula I also contain several basic groups (e.g., amino groups) and therefore, the compounds of formula I can exist as the free base or in various salt forms. All such salt forms are included within the scope of this invention. Furthermore, solvates of compounds of formula I or salts thereof are included within the scope of this invention.

Additionally, where applicable, all cis-trans or E/Z isomers (geometric isomers), tautomeric forms and topoisomeric forms of the compounds of formula I are included within the scope of this invention unless otherwise specified.

The compounds of formula I, as well as those compounds used in its synthesis, may also include isotopically-labeled compounds, i.e., where one or more atoms have been enriched with atoms having an atomic mass different from the atomic mass predominately found in nature. Examples of isotopes that may be incorporated into the compounds of Formula (I) include, but are not limited to, $^2$H, $^3$H, $^{13}$C, $^{14}$C, $^{15}$N, $^{18}$O and $^{17}$O.

The nomenclature used herein to name the compounds of this invention is illustrated in the Examples herein. This nomenclature has generally been derived using the commercially-available AutoNom software (MDL, San Leandro, Calif.).

Representative Embodiments

The following substituents and values are intended to provide representative examples of various aspects and embodiments of this invention. These representative values are intended to further define and illustrate such aspects and embodiments and are not intended to exclude other embodiments or to limit the scope of this invention. In this regard, the representation that a particular value or substituent is preferred is not intended in any way to exclude other values or substituents from this invention unless specifically indicated.

The values for a and b are independently 0, 1, 2, 3, 4 or 5; particularly independently 0, 1 or 2; and even more particularly 0 or 1. In one embodiment, both a and b are 0.

When present, each $R^1$ and $R^2$ may be at the 2, 3, 4, 5 or 6-position of the phenyl ring to which it is attached. Each $R^1$ and $R^2$ are independently selected from (1-4C)alkyl, (2-4C)alkenyl, (2-4C)alkynyl, (3-6C)cycloalkyl, cyano, halo, —$OR^a$, —$SR^a$, —$NR^aR^b$, —$S(O)R^c$ and —$S(O)_2R^c$. Each $R^a$ and $R^b$ independently represents hydrogen, (1-4C)alkyl, (2-4C)alkenyl, (2-4C)alkynyl or (3-6C)cycloalkyl. Each $R^c$ independently represents (1-4C)alkyl, (2-4C)alkenyl, (2-4C)alkynyl or (3-6C)cycloalkyl. Alternatively, two adjacent $R^1$ groups or two adjacent $R^2$ groups may be joined together to form (3-6C)alkylene, (2-4C)alkylene-O— or —O-(2-4C)alkylene-O—. In addition, each alkyl group in $R^1$, $R^2$, and $R^{a-c}$ is optionally substituted with from 1 to 5 fluoro substituents, and in one embodiment optionally substituted with 1 to 3 fluoro substituents. In a specific embodiment, $R^1$ or $R^2$ are independently selected from (1-4C)alkyl, fluoro, chloro and —$OR^a$. In another specific embodiment, each $R^1$ and $R^2$ is (1-2C)alkyl or fluoro. Representative $R^1$ and $R^2$ groups include, but are not limited to, methyl, ethyl, n-propyl, isopropyl, difluoromethyl, trifluoromethyl, 2,2,2-trifluoroethyl, fluoro, chloro, methoxy, ethoxy, difluoromethoxy and trifluoromethoxy.

The value for c is 0, 1, 2, or 3; particularly 0, 1 or 2; and even more particularly 0 or 1. A particular value for c is 0. Particular mention is made of compounds in which each of a, b and c represents 0.

When present, each $R^3$ independently is fluoro or (1-4C) alkyl. In addition, each alkyl group in $R^3$ is optionally substituted with from 1 to 5 fluoro substituents, and in one embodiment optionally substituted with 1 to 3 fluoro substituents. In a specific embodiment, each $R^3$ is independently selected from (1-2C)alkyl and fluoro. When two $R^3$ substituents are present (c=2), they can be on the same or different carbon atoms. Representative $R^3$ groups include, but are not limited to, methyl, ethyl, difluoromethyl, trifluoromethyl and fluoro.

$R^{4a}$ and $R^{4b}$ are independently selected from hydrogen, (1-4C)alkyl, and phenyl-(1-4C)alkyl. $R^{4a}$ and $R^{4b}$ together with the nitrogen atom to which they are attached may form a (3-6C)heterocyclic ring optionally containing one additional heteroatom selected from nitrogen, oxygen or sulfur. This heterocyclic ring is unsubstituted or substituted with 1 or 2 substituents selected independently from (1-4C)alkyl and fluoro. In addition, each alkyl group in $R^{4a}$ and $R^{4b}$ is optionally substituted with from 1 to 5 fluoro substituents, and in one embodiment optionally substituted with 1 to 3 fluoro substituents. In one embodiment, $R^{4a}$ and $R^{4b}$ are independently hydrogen or (1-4C)alkyl. In another embodiment $R^{4a}$ and $R^{4b}$ are independently hydrogen or (1-2C) alkyl, such as methyl and ethyl. In yet another embodiment, $R^{4a}$ and $R^{4b}$ are both hydrogen. Alternatively, in another specific embodiment, $R^{4a}$ and $R^{4b}$ are joined together with the nitrogen atom to which they are attached to form a (3-5C)heterocyclic ring optionally containing one additional heteroatom selected from nitrogen, oxygen or sulfur. Representative heterocyclic rings include, but are not limited to, pyrrolidin-1-yl, piperidin-1-yl, piperazin-1-yl, 4-(1-4C) alkylpiperazin-1-yl, morpholin-4-yl and thiomorpholin-4-yl.

The value for e is 1 or 2. In one embodiment, e is 1.

The value for m is 1, 2, 3 or 4. In one embodiment, m is 2, 3 or 4. In another embodiment, m is 2 or 3.

$Ar^1$ represents a phenylene group or a (3-5C)heteroarylene group containing 1 or 2 heteroatoms selected independently from oxygen, nitrogen or sulfur. The phenylene and heteroarylene groups are unsubstituted or substituted with 1 to 4 substituents selected independently from halo, (1-4C)alkyl or (1-4C)alkoxy; where each alkyl and alkoxy group is optionally substituted with from 1 to 3 fluoro substituents;

In one embodiment $Ar^1$ is phen-1,3-ylene or phen-1,4-ylene wherein the phenylene group is unsubstituted or substituted with 1, 2 or 3 substituents selected independently from halo, (1-4C)alkyl or (1-4C)alkoxy, wherein each alkyl and alkoxy group is optionally substituted with from 1 to 3 fluoro substituents. Representative substituents include fluoro, chloro, methyl, ethyl, n-propyl, isopropyl, n-butyl, isobutyl, sec-butyl, tert-butyl, methoxy, ethoxy, isopropoxy, difluoromethyl, trifluoromethyl, 2,2,2-trifluoroethyl and trifluoromethoxy. Particular examples of $Ar^1$ groups in this embodiment include 2-fluorophen-1,4-ylene, 3-fluorophen-1,4-ylene, 2-chlorophen-1,4-ylene, 3-chlorophen-1,4-ylene, 2-methylphen-1,4-ylene, 3-methylphen-1,4-ylene, 2-methoxyphen-1,4-ylene, 3-methoxyphen-1,4-ylene, 2-trifluoromethoxyphen-1,4-ylene, 3-trifluoromethoxyphen-1,4-ylene, 2,3-difluorophen-1,4-ylene, 2,5-difluorophen-1,4-ylene, 2,6-difluorophen-1,4-ylene, 2,3-dichlorophen-1,4-ylene, 2,5-dichlorophen-1,4-ylene, 2,6-dichlorophen-1,4-ylene, 2-chloro-5-methoxyphen-1,4-ylene, 2-chloro-6-methoxyphen-1,4-ylene, 2-chloro-5-trifluoromethoxyphen-1,4-ylene and 2-chloro-6-trifluoromethoxyphen-1,4-ylene.

In another embodiment, $Ar^1$ is a (3-5C)heteroarylene group containing 1 or 2 heteroatoms selected independently from oxygen, nitrogen or sulfur; wherein the heteroarylene group is unsubstituted or substituted with 1 or 2 substituents selected independently from halo, (1-4C)alkyl or (1-4C) alkoxy; wherein each alkyl and alkoxy group is optionally substituted with from 1 to 3 fluoro substituents. Representative heteroarylene groups include divalent species of pyrrole, imidazole, thiazole, oxazole, furan, thiophene, pyrazole, isoxazole, isothiazole, pyridine, pyrazine, pyridazine and pyrimidine, where the point of attachment is at any available carbon or nitrogen ring atom. More specific examples of such $Ar^1$ groups include 2,5-furylene, 2,4-thienylene, 2,5-thienylene, 2,5-pyridylene, 2,6-pyridylene, and 2,5-pyrrolylene. Representative $R^5$ substituents include fluoro, chloro, methyl, ethyl, n-propyl, isopropyl, n-butyl, isobutyl, sec-butyl, tert-butyl, methoxy, ethoxy, isopropoxy, difluoromethyl, trifluoromethyl, 2,2,2-trifluoroethyl and trifluoromethoxy. Particular examples of substituted $Ar^1$ groups include 3-fluoro-2,5-thienylene, 3-chloro-2,5-thienylene, 3-methyl-2,5-thienylene, 3-methoxy-2,5-thienylene, and 3-methoxy-6-chloro-2,5-pyridylene.

The value for n is 0, 1, 2, 3 or 4. In one embodiment, n is 0, 2 or 3. In another embodiment, n is 2 or 3.

The values of m, n and $Ar^1$ are selected such that the number of contiguous atoms in the chain —$(CH_2)_m$—$Ar^1$—$(CH_2)_n$— between the two nitrogen atoms to which it is attached is in the range of from 7 to 12;

$R^5$ is selected from hydrogen, (1-6C)alkyl, $Ar^2$, —$CH_2Ar^2$ and —$CH_2CH_2NHC(O)R^{5a}$. $Ar^2$ represents phenyl, (3-6C)cycloalkyl or (3-5C)heteroaryl containing 1 or 2 heteroatoms selected from oxygen, nitrogen or sulfur, where the phenyl and heteroaryl groups are unsubstituted or substituted with 1 to 3 substituents selected independently from halo, (1-4C)alkyl, (1-4C)alkoxy and methylenedioxy. $R^{5a}$ represents (1-4C)alkyl. In addition, each alkyl group in $R^5$ is optionally substituted with from 1 to 5 fluoro substituents, and in one embodiment optionally substituted with 1 to 3 fluoro substituents. In a specific embodiment, $R^5$ is hydrogen or (1-4C)alkyl, for example hydrogen, methyl, ethyl, n-propyl, isopropyl, n-butyl, isobutyl, sec-butyl and tert-butyl. In another embodiment, $R^5$ is $Ar^2$, where $Ar^2$ is (3-6C)cycloalkyl, such as cyclopropyl, cyclobutyl and cyclopentyl. In yet another embodiment, $R^5$ is —$CH_2Ar^2$, where $Ar^2$ is a phenyl, furyl, thienyl, pyridyl or pyrazinyl group that is optionally substituted as described above, for example, 3,4-methylenedioxyphenylmethyl, fur-2-ylmethyl and 5-methylpyrazin-2-ylmethyl. In still another embodiment, $R^5$ is —$CH_2CH_2NHCOR^{5a}$, such as —$CH_2CH_2NHCOCH_3$. An example of a particular value for $R^{5a}$ is methyl.

$R^6$ is hydrogen or (1-6C)alkyl, including hydrogen, methyl, ethyl, n-propyl, isopropyl, n-butyl, isobutyl, sec-butyl and tert-butyl. In addition, each alkyl group in $R^6$ is optionally substituted with from 1 to 5 fluoro substituents, and in one embodiment optionally substituted with 1 to 3 fluoro substituents. In a specific embodiment, $R^6$ is hydrogen or methyl.

Alternatively, $R^5$ and $R^6$ together with the nitrogen atom to which they are attached form a (3-5C)azacycloalkyl group, examples of which include, azetidin-1-yl, pyrrolidin-1-yl and piperidin-1-yl groups. In addition, when $Ar^1$ represents heteroarylene, such as thienylene, $R^5$ and $R^6$ together with the nitrogen atom to which they are attached can form a morpholin-1-yl or 4-(1-6C)alkylpiperazin-1-yl group.

A particular group of compounds of interest are compounds of formula I wherein a and b are 0. Another group of compounds of interest are compounds of formula I wherein a, b and c are 0. A particular group of compounds of interest are compounds of formula I wherein a, b and c are 0; and $R^{4a}$ and $R^{4b}$ are hydrogen. Another particular group of compounds of interest are compounds of formula I wherein a, b and c are 0; $R^{4a}$ and $R^{4b}$ are hydrogen; and $R^5$ is (1-4C)alkyl. Another particular group of interest are compounds of formula I wherein a, b and c are 0; $R^{4a}$ and $R^{4b}$ are hydrogen; $R^5$ is (1-4C)alkyl; and $R^6$ is hydrogen or methyl. Another particular group of compounds of interest are compounds of formula I wherein a, b and c are 0; $R^{4a}$ and $R^{4b}$ are hydrogen; and $R^5$ and $R^6$ are joined together with nitrogen to which they are attached to form a (3-5C)azacycloalkyl group.

Another particular group of compounds of interest are compounds of formula I, where a, b, and c are 0; $R^{4a}$ and $R^{4b}$ are hydrogen; e is 1; and $Ar^1$ is phen-1,4-ylene. These compounds have the formula Ia:

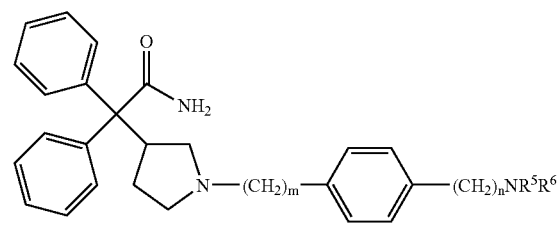

Ia where m, n, $R^5$ and $R^6$ are as defined herein; where m+n is an integer from 3 to 8; and where the phen-1,4-ylene group is optionally substituted with 1 to 4 substituents as defined herein for $Ar^1$; or a pharmaceutically acceptable salt or solvate or stereoisomer thereof.

Another particular group of compounds of interest are compounds of formula I, where a, b, and c are 0; $R^{4a}$ and $R^{4b}$ are hydrogen; e is 1; and $Ar^1$ is phen-1,3-ylene. These compounds have the formula Ib:

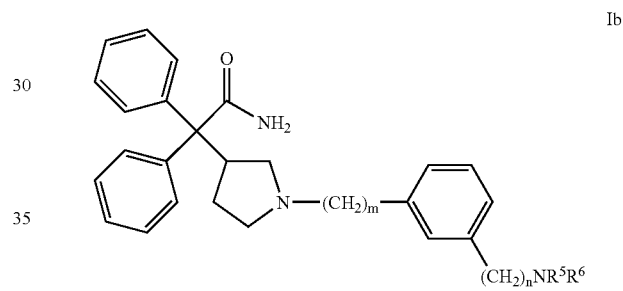

Ib where m, n, $R^5$ and $R^6$ are as defined herein; where m+n is an integer from 4 to 9; and where the phen-1,3-ylene group is optionally substituted with 1 to 4 substituents as defined herein for $Ar^1$; or a pharmaceutically acceptable salt or solvate or stereoisomer thereof.

Another particular group of compounds of interest are compounds of formula I, where a, b, and c are 0; $R^{4a}$ and $R^{4b}$ are hydrogen; e is 1; and $Ar^1$ is 2,5-thiophene. These compounds have the formula Ic:

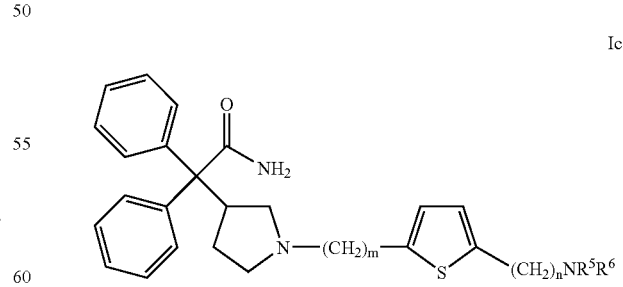

Ic where m, n, $R^5$ and $R^6$ are as defined herein; where m+n is an integer from 4 to 9; and where the 2,5-thienylene group is optionally substituted with 1 to 2 substituents as defined herein for $Ar^1$; or a pharmaceutically acceptable salt or solvate or stereoisomer thereof.

Another particular group of compounds of interest are compounds of formula I, where a, b, and c are 0; $R^{4a}$ and $R^{4b}$ are hydrogen; and e is 1. These compounds have the formula Id:

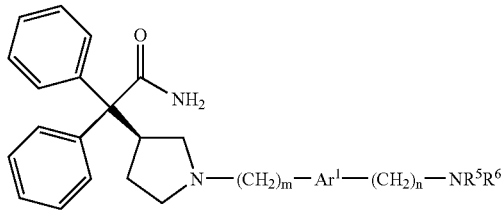

Id where $Ar^1$, $R^5$, $R^6$, m and n are as defined in Table I; or a pharmaceutically acceptable salt or solvate thereof.

TABLE I

| Ex. | m | $Ar^1$ | n | $R^5$ | $R^6$ |
|---|---|---|---|---|---|
| 1 | 4 | phen-1,4-ylene | 0 | H | H |
| 2 | 2 | phen-1,4-ylene | 2 | —CH₃ | H |
| 3 | 2 | phen-1,3-ylene | 2 | —CH₃ | H |
| 4 | 3 | 2,5-thienylene | 3 | —CH₃ | H |
| 5 | 3 | phen-1,3-ylene | 3 | —CH₃ | H |
| 6 | 3 | phen-1,4-ylene | 2 | —CH₃ | H |
| 7 | 3 | 2,5-thienylene | 3 | —CH₂CH₃ | H |
| 8 | 3 | 2,5-thienylene | 3 | —CH(CH₃)₂ | H |
| 9 | 3 | 2,5-thienylene | 3 | —CH₃ | —CH₃ |
| 10 | 2 | phen-1,4-ylene | 2 | —CH₂CH₃ | H |
| 11 | 2 | phen-1,4-ylene | 2 | —CH(CH₃)₂ | H |
| 12 | 2 | phen-1,4-ylene | 2 | —CH₃ | —CH₃ |
| 13 | 2 | phen-1,4-ylene | 2 | —(CH₂)₄—* | |
| 14 | 2 | phen-1,4-ylene | 2 | —CH₂-phenyl | —CH₃ |
| 15 | 2 | phen-1,4-ylene | 2 | —CH₂CH₂NHC(O)CH₃ | H |
| 16 | 2 | phen-1,4-ylene | 2 | —CH₂-(5-methylpyrazin-2-yl) | H |
| 17 | 2 | phen-1,4-ylene | 2 | —CH₂-(furan-2-yl) | H |
| 18 | 2 | phen-1,4-ylene | 2 | —CH₂-(3,4-methylenedioxy-phenyl) | H |
| 19 | 2 | phen-1,4-ylene | 2 | —(CH₂)₃—* | |
| 20 | 3 | 2,5-thienylene | 3 | —CH₂CH₂NHC(O)CH₃ | H |
| 21 | 3 | 2,5-thienylene | 3 | —CH₂-(5-methylpyrazin-2-yl) | H |
| 22 | 3 | 2,5-thienylene | 3 | —CH₂-(furan-2-yl) | H |
| 23 | 3 | 2,5-thienylene | 3 | —CH₂-(3,4-methylenedioxy-phenyl) | H |
| 24 | 3 | 2,5-thienylene | 3 | —(CH₂CH₂N(CH₃)CH₂CH₂—* | |
| 25 | 3 | 2,5-thienylene | 3 | —(CH₂CH₂OCH₂CH₂—* | |
| 26 | 3 | 2,5-thienylene | 3 | —(CH₂)₃—* | |

*In these compounds, $R^5$ and $R^6$ are joined together to form the group indicated.

Definitions

When describing the compounds, compositions, methods and processes of this invention, the following terms have the following meanings unless otherwise indicated.

The term "alkyl" means a monovalent saturated hydrocarbon group which may be linear or branched. Unless otherwise defined, such alkyl groups typically contain from 1 to 10 carbon atoms. Representative alkyl groups include, by way of example, methyl, ethyl, n-propyl, isopropyl, n-butyl, sec-butyl, isobutyl, tert-butyl, n-pentyl, n-hexyl, n-heptyl, n-octyl, n-nonyl, n-decyl and the like.

The term "alkylene" means a divalent saturated hydrocarbon group which may be linear or branched. Unless otherwise defined, such alkylene groups typically contain from 1 to 10 carbon atoms. Representative alkylene groups include, by way of example, methylene, ethane-1,2-diyl ("ethylene"), propane-1,2-diyl, propane-1,3-diyl, butane-1,4-diyl, pentane-1,5-diyl and the like.

The term "alkoxy" means a monovalent group of the formula (alkyl)-O—, where alkyl is as defined herein. Representative alkoxy groups include, by way of example, methoxy, ethoxy, n-propoxy, isopropoxy, n-butoxy, isobutoxy, tert-butoxy and the like.

The term "alkenyl" means a monovalent unsaturated hydrocarbon group which may be linear or branched and which has at least one, and typically 1, 2 or 3, carbon-carbon double bonds. Unless otherwise defined, such alkenyl groups typically contain from 2 to 10 carbon atoms. Representative alkenyl groups include, by way of example, ethenyl, n-propenyl, isopropenyl, n-but-2-enyl, n-hex-3-enyl and the like. The term "alkenylene" means a divalent alkenyl group.

The term "alkynyl" means a monovalent unsaturated hydrocarbon group which may be linear or branched and which has at least one, and typically 1, 2 or 3, carbon-carbon triple bonds. Unless otherwise defined, such alkynyl groups typically contain from 2 to 10 carbon atoms. Representative alkynyl groups include, by way of example, ethynyl, n-propynyl, n-but-2-ynyl, n-hex-3-ynyl and the like. The term "alkynylene" means a divalent alkynyl group.

The term "aryl" means a monovalent aromatic hydrocarbon having a single ring (i.e., phenyl) or fused rings (i.e., naphthalene). Unless otherwise defined, such aryl groups typically contain from 6 to 10 carbon ring atoms. Representative aryl groups include, by way of example, phenyl and naphthalene-1-yl, naphthalene-2-yl, and the like. The term "arylene" means a divalent aryl group.

The term "azacycloalkyl" means a monovalent heterocyclic ring containing one nitrogen atom, i.e., a cycloalkyl group in which one carbon atom has been replaced with a nitrogen atom. Unless otherwise defined, such azacycloalkyl groups typically contain from 2 to 9 carbon atoms. Representative examples of an azacycloalkyl group are pyrrolidinyl and piperidinyl groups. The term "azacycloalkylene" means a divalent azacycloakyl group. Representative examples of an azacycloalkylene group are pyrrolidinylene and piperidinylene groups.

The term "cycloalkyl" means a monovalent saturated carbocyclic hydrocarbon group. Unless otherwise defined, such cycloalkyl groups typically contain from 3 to 10 carbon atoms. Representative cycloalkyl groups include, by way of example, cyclopropyl, cyclobutyl, cyclopentyl, cyclohexyl and the like. The term "cycloalkylene" means a divalent cycloalkyl group.

The term "halo" means fluoro, chloro, bromo and iodo.

The term "heteroaryl" means a monovalent aromatic group having a single ring or two fused rings and containing in the ring at least one heteroatom (typically 1 to 3 heteroatoms) selected from nitrogen, oxygen or sulfur. Unless otherwise defined, such heteroaryl groups typically contain from 5 to 10 total ring atoms. Representative heteroaryl groups include, by way of example, monovalent species of pyrrole, imidazole, thiazole, oxazole, furan, thiophene, triazole, pyrazole, isoxazole, isothiazole, pyridine, pyrazine, pyridazine, pyrimidine, triazine, indole, benzofuran, benzothiophene, benzimidazole, benzthiazole, quinoline, isoquinoline, quinazoline, quinoxaline and the like, where the point of attachment is at any available carbon or nitrogen ring atom. The term "heteroarylene" means a divalent heteroaryl group.

The term "heterocyclyl" or "heterocyclic" means a monovalent saturated or unsaturated (non-aromatic) group having a single ring or multiple condensed rings and containing in the ring at least one heteroatom (typically 1 to 3 heteroatoms) selected from nitrogen, oxygen or sulfur. Unless otherwise defined, such heterocyclic groups typically contain from 2 to 9 total ring carbon atoms. Representative heterocyclic groups include, by way of example, monovalent species of pyrrolidine, imidazolidine, pyrazolidine, piperidine, 1,4-dioxane, morpholine, thiomorpholine, piperazine, 3-pyrroline and the like, where the point of attachment is at any available carbon or nitrogen ring atom. The term "heterocyclene" means a divalent heterocyclyl or heterocyclic group.

When a specific number of carbon atoms is intended for a particular term used herein, the number of carbon atoms is shown in parentheses preceding the term. For example, the term "(1-4C)alkyl" means an alkyl group having from 1 to 4 carbon atoms.

The term "pharmaceutically acceptable salt" means a salt which is acceptable for administration to a patient, such as a mammal (e.g., salts having acceptable mammalian safety for a given dosage regime). Such salts can be derived from pharmaceutically acceptable inorganic or organic bases and from pharmaceutically acceptable inorganic or organic acids. Salts derived from pharmaceutically acceptable inorganic bases include ammonium, calcium, copper, ferric, ferrous, lithium, magnesium, manganic, manganous, potassium, sodium, zinc and the like. Particularly preferred are ammonium, calcium, magnesium, potassium and sodium salts. Salts derived from pharmaceutically acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from pharmaceutically acceptable acids include acetic, ascorbic, benzenesulfonic, benzoic, camphosulfonic, citric, ethanesulfonic, edisylic, fumaric, gentisic, gluconic, glucoronic, glutamic, hippuric, hydrobromic, hydrochloric, isethionic, lactic, lactobionic, maleic, malic, mandelic, methanesulfonic, mucic, naphthalenesulfonic, naphthalene-1,5-disulfonic, naphthalene-2,6-disulfonic, nicotinic, nitric, orotic, pamoic, pantothenic, phosphoric, succinic, sulfuric, tartaric, p-toluenesulfonic, xinafoic and the like. Particularly preferred are citric, hydrobromic, hydrochloric, isethionic, maleic, naphthalene-1,5-disulfonic, phosphoric, sulfuric and tartaric acids.

The term "salt thereof" means a compound formed when the hydrogen of an acid is replaced by a cation, such as a metal cation or an organic cation and the like. Preferably, the salt is a pharmaceutically acceptable salt, although this is not required for salts of intermediate compounds that are not intended for administration to a patient.

The term "solvate" means a complex or aggregate formed by one or more molecules of a solute, i.e. a compound of formula I or a pharmaceutically acceptable salt thereof, and one or more molecules of a solvent. Such solvates are typically crystalline solids having a substantially fixed molar ratio of solute and solvent. Representative solvents include, by way of example, water, methanol, ethanol, isopropanol, acetic acid and the like. When the solvent is water, the solvate formed is a hydrate.

It will be appreciated that the term "or a pharmaceutically acceptable salt or solvate or stereoisomer thereof" is intended to include all permutations of salts, solvates and stereoisomers, such as a solvate of a pharmaceutically acceptable salt of a stereoisomer of a compound of formula I.

The term "therapeutically effective amount" means an amount sufficient to effect treatment when administered to a patient in need of treatment.

The term "treating" or "treatment" as used herein means the treating or treatment of a disease or medical condition (such as COPD) in a patient, such as a mammal (particularly a human) that includes:
(a) preventing the disease or medical condition from occurring, i.e., prophylactic treatment of a patient;
(b) ameliorating the disease or medical condition, i.e., eliminating or causing regression of the disease or medical condition in a patient;
(c) suppressing the disease or medical condition, i.e., slowing or arresting the development of the disease or medical condition in a patient; or
(d) alleviating the symptoms of the disease or medical condition in a patient.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The term "protected derivatives thereof" means a derivative of the specified compound in which one or more functional groups of the compound are protected from undesired reactions with a protecting or blocking group. Functional groups which may be protected include, by way of example, carboxylic acid groups, amino groups, hydroxyl groups, thiol groups, carbonyl groups and the like. Representative protecting groups for carboxylic acids include esters (such as a p-methoxybenzyl ester), amides and hydrazides; for amino groups, carbamates (such as tert-butoxycarbonyl) and amides; for hydroxyl groups, ethers and esters; for thiol groups, thioethers and thioesters; for carbonyl groups, acetals and ketals; and the like. Such protecting groups are well-known to those skilled in the art and are described, for example, in T. W. Greene and G. M. Wuts, *Protecting Groups in Organic Synthesis*, Third Edition, Wiley, N.Y., 1999, and references cited therein.

The term "amino-protecting group" means a protecting group suitable for preventing undesired reactions at an amino group. Representative amino-protecting groups include, but are not limited to, tert-butoxycarbonyl (BOC), trityl (Tr), benzyloxycarbonyl (Cbz), 9-fluorenylmethoxycarbonyl (Fmoc), formyl, trimethylsilyl (TMS), tert-butyldimethylsilyl (TBS), and the like.

The term "carboxy-protecting group" means a protecting group suitable for preventing undesired reactions at a carboxy group. Representative carboxy-protecting groups include, but are not limited to, esters, such as methyl, ethyl, tert-butyl, benzyl (Bn), p-methoxybenzyl (PMB), 9-fluroenylmethyl (Fm), trimethylsilyl (TMS), tert-butyldimethylsilyl (TBS), diphenylmethyl (benzhydryl, DPM) and the like.

The term "hydroxyl-protecting group" means a protecting group suitable for preventing undesirable reactions at a hydroxyl group. Representative hydroxyl-protecting groups include, but are not limited to, silyl groups including tri(1-6C)alkylsilyl groups, such as trimethylsilyl (TMS), triethylsilyl (TES), tert-butyldimethylsilyl (TBS) and the like; esters (acyl groups) including (1-6C)alkanoyl groups, such as formyl, acetyl and the like; arylmethyl groups, such as benzyl (Bn), p-methoxybenzyl (PMB), 9-fluorenylmethyl (Fm), diphenylmethyl (benzhydryl, DPM) and the like. Additionally, two hydroxyl groups can also be protected as an alkylidene group, such as prop-2-ylidine, formed, for example, by reaction with a ketone, such as acetone.

General Synthetic Procedures

The diphenylmethyl compounds of this invention can be prepared from readily available starting materials using the following general methods and procedures or by using other information readily available to those of ordinary skill in the art. Although a particular embodiment of the present invention may be shown or described herein, those skilled in the art will recognize that all embodiments or aspects of the present invention can be prepared using the methods described herein or by using other methods, reagents and starting materials known to those skilled in the art. It will also be appreciated that where typical or preferred process conditions (i.e., reaction temperatures, times, mole ratios of reactants, solvents, pressures, etc.) are given, other process conditions can also be used unless otherwise stated. While the optimum reaction conditions may vary depending on the particular reactants or solvent used, such conditions can be readily determined by one skilled in the art by routine optimization procedures.

Additionally, as will be apparent to those skilled in the art, conventional protecting groups may be necessary or desired to prevent certain functional groups from undergoing undesired reactions. The choice of a suitable protecting group for a particular functional group as well as suitable conditions for protection and deprotection of such functional groups are well-known in the art. Protecting groups other than those illustrated in the procedures described herein may be used, if desired. For example, numerous protecting groups, and their introduction and removal, are described in T. W. Greene and G. M. Wuts, *Protecting Groups in Organic Synthesis*, Third Edition, Wiley, N.Y., 1999, and references cited therein.

By way of illustration, the compounds of formula I can be prepared by a process comprising:
(a) reacting a compound of formula II:

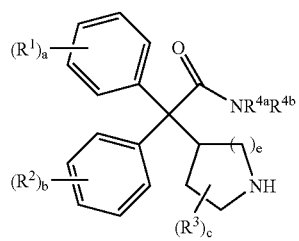

II with a compound of formula III:

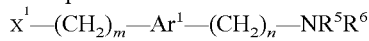

III wherein $X^1$ represents a leaving group;
(b) reacting a compound of formula IV:

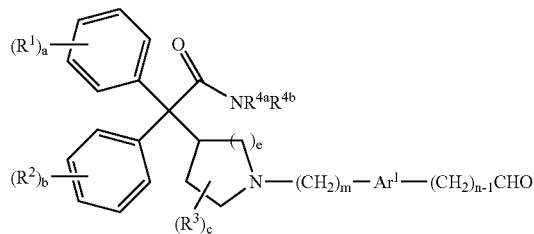

IV with a compound of formula V:

V in the presence of a reducing agent;

(c) reacting a compound of formula VI:

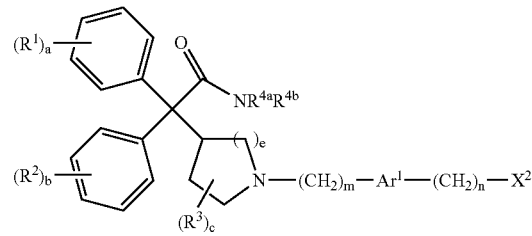

VI wherein $X^2$ represents a leaving group, with a compound of formula V;
(d) reacting a compound of formula II with a compound of formula VII:

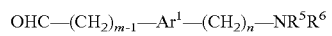

VII in the presence of a reducing agent; or
(e) reacting a compound of formula VIII:

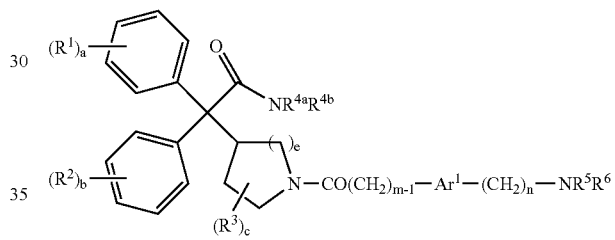

VIII with a reducing agent; to provide a compound of formula I; and optionally, forming a pharmaceutically acceptable salt or solvate or stereoisomer thereof.

In these reactions, depending upon the particular substituents present, one or more protecting groups may be employed. If such protecting groups are used, they are removed using conventional procedures to provide the compound of formula I.

Generally, if a salt of one of the starting materials is used in the processes described above, such as an acid addition salt, the salt is typically neutralized before or during the reaction process. This neutralization reaction is typically accomplished by contacting the salt with one molar equivalent of a base for each molar equivalent of acid addition salt.

In process (a), the reaction between the compounds of formula II and III, the leaving group represented by $X^1$ can be, for example, halo, such as chloro, bromo or iodo, or a sulfonic ester group, such as mesylate or tosylate. The reaction is conveniently performed in the presence of a base, for example, a tertiary amine such as diisopropylethylamine. Convenient solvents include nitriles, such as acetonitrile. The reaction is conveniently conducted at a temperature in the range of from 0° C. to 100° C.

Compounds of formula II may be prepared as described in U.S. Pat. No. 5,096,890 to Cross et al., the disclosure of which is incorporated herein by reference in its entirety. Alternatively, compounds of formula II can be prepared by deprotecting a compound of formula IX:

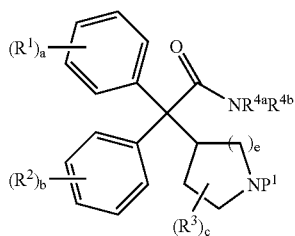

IX in which $P^1$ represents an amino-protecting group, such as a benzyl group. Benzyl groups are conveniently removed by reduction, for example, using a hydrogen or ammonium formate and a Group VIII metal catalyst, such as palladium.

Compounds of formula IX can be prepared by reacting a carboxylic acid of formula X:

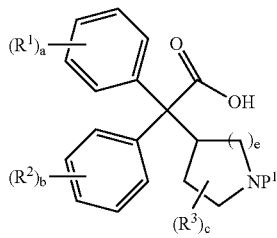

X with an amine of formula $HNR^{4a}R^{4b}$ under amide bond forming conditions.

Compounds of formula X may be prepared by hydrolyzing a compound of formula XI:

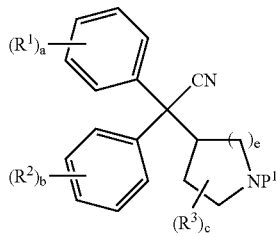

XI

Compounds of formula XI can be prepared as described in U.S. Pat. No. 5,096,890 to Cross et al.

Compounds of formula III are generally known or can be prepared from readily available starting materials using well-known synthetic methods.

In process (b), the reducing agent can be, for example, hydrogen in the presence of a Group VIII metal catalyst, such as palladium, or a metal hydride reducing agent, such as sodium triacetoxyborohydride. The reaction is conveniently performed at a temperature in the range of from 0° C. to 100° C. Convenient solvents include halogenated hydrocarbons, such as dichloroethane and alcohols, such as methanol.

Compounds of formula IV can be prepared by oxidizing a compound of formula XII:

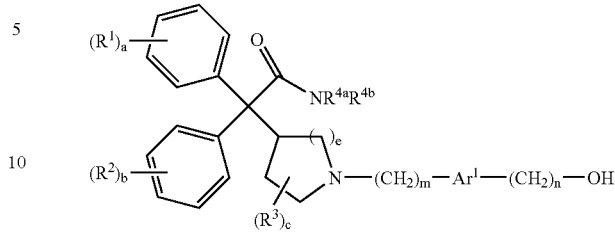

XII using a suitable oxidizing agent, such as sulfur trioxide pyridine complex in dimethyl sulfoxide in the presence of a tertiary amine base, such as diisopropylethylamine.

Compounds of formula XII can be prepared by reacting a compound of formula II with a compound of formula XIII:

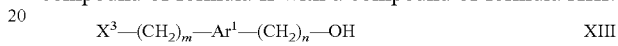

$$X^3-(CH_2)_m-Ar^1-(CH_2)_n-OH \qquad \text{XIII}$$

in which $X^3$ represents a leaving group including, for example, halo, such as chloro, bromo or iodo, or a sulfonic ester group, such as mesylate or tosylate.

In process (c), the reaction between the compounds of formula VI and V, the leaving group represented by $X^2$ can be, for example, halo, such as chloro, bromo or iodo, or a sulfonic ester group, such as mesylate or tosylate. The reaction is conveniently performed in the presence of a base such as a tertiary amine, including diisopropylethylamine, or an alkali metal carbonate, such as potassium carbonate. Convenient solvents include nitrites, such as acetonitrile and amides, such as dimethylformamide. The reaction is conveniently conducted at a temperature in the range of from 0° C. to 100° C.

Compounds of formula VI can be prepared by reacting a compound of formula XII with an appropriate reagent, for example, a halogenating agent such as thionyl chloride. Alternatively, such compounds can be prepared by reacting a compound of formula II with a compound of formula XIV:

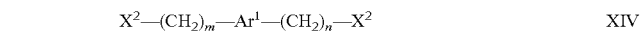

$$X^2-(CH_2)_m-Ar^1-(CH_2)_n-X^2 \qquad \text{XIV}$$

The compounds of formula XIV may conveniently be prepared by reacting the corresponding diol with a halogenating agent. For example, compounds of formula XIV in which $X^2$ represents bromine may be prepared by reacting the corresponding diol with a brominating agent, such as hydrogen bromide or dibromotriphenylphosporane.

In process (d), the reducing agent can be, for example, hydrogen in the presence of a Group VIII metal catalyst, such as palladium, or a metal hydride reducing agent, such as sodium triacetoxyborohydride. The reaction is conveniently performed at a temperature in the range of from 0° C. to 100° C. Convenient solvents include halogenated hydrocarbons, such as dichloroethane and alcohols, such as methanol. Compounds of formula VII can be prepared by oxidizing a compound of formula XV:

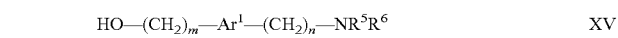

$$HO-(CH_2)_m-Ar^1-(CH_2)_n-NR^5R^6 \qquad \text{XV}$$

using a suitable oxidizing agent, such as sulfur trioxide pyridine complex in dimethyl sulfoxide in the presence of a tertiary amine base, such as diisopropylethylamine.

In process (e), the reducing agent can be, for example, a metal hydride reducing agent, such as diisobutylaluminium hydride (DIBAL). The reaction is conveniently performed at a temperature in the range of from 0° C. to 100° C. Suitable solvents include ethers, such as tetrahydrofuran. Compounds of formula VIII can be prepared by reacting a compound of formula II with a compound of formula XVI:

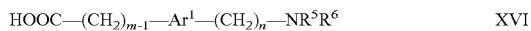
$$HOOC-(CH_2)_{m-1}-Ar^1-(CH_2)_n-NR^5R^6 \qquad XVI$$

or a reactive derivative thereof, such as an anhydride. The reaction may be conducted under conventional amide bond-forming conditions.

It will be appreciated that certain compounds of formula I, for example those in which $R^5$ represents $-(CH_2)Ar^2$, such as benzyl, may themselves serve as intermediates for other compounds of formula I. Thus, a $-(CH_2)Ar^2$ group may serve as a protecting group and may be removed by catalytic hydrogenation, for example, in the presence of palladium on carbon.

Certain of the intermediates described herein are believed to be novel and accordingly, such compounds are provided as further aspects of the invention including, for example, the compounds of formula IV, VI and VIII and salts thereof.

Further details regarding specific reaction conditions and other procedures for preparing representative compounds of this invention or intermediates thereof are described in the Examples set forth below.

Pharmaceutical Compositions and Formulations

The diphenylmethyl compounds of this invention are typically administered to a patient in the form of a pharmaceutical composition or formulation. Such pharmaceutical compositions may be administered to the patient by any acceptable route of administration including, but not limited to, inhaled, oral, nasal, topical (including transdermal) and parenteral modes of administration. It will be understood that any form of the compounds of this invention, (i.e., free base, pharmaceutically acceptable salt, solvate, etc.) that is suitable for the particular mode of administration can be used in the pharmaceutical compositions discussed herein.

Accordingly, in one of its composition aspects, this invention is directed to a pharmaceutical composition comprising a pharmaceutically acceptable carrier or excipient and a therapeutically effective amount of a compound of formula I, or a pharmaceutically acceptable salt or solvate or stereoisomer thereof. Optionally, such pharmaceutical compositions may contain other therapeutic and/or formulating agents if desired.

The pharmaceutical compositions of this invention typically contain a therapeutically effective amount of a compound of the present invention or a pharmaceutically acceptable salt or solvate or stereoisomer thereof. Typically, such pharmaceutical compositions will contain from about 0.01 to about 95% by weight of the active agent; including, from about 0.01 to about 30% by weight; such as from about 0.01 to about 10% by weight of the active agent.

Any conventional carrier or excipient may be used in the pharmaceutical compositions of this invention. The choice of a particular carrier or excipient, or combinations of carriers or excipients, will depend on the mode of administration being used to treat a particular patient or type of medical condition or disease state. In this regard, the preparation of a suitable pharmaceutical composition for a particular mode of administration is well within the scope of those skilled in the pharmaceutical arts. Additionally, the ingredients for such compositions are commercially available from, for example, Sigma, P.O. Box 14508, St. Louis, Mo. 63178. By way of further illustration, conventional formulation techniques are described in *Remington: The Science and Practice of Pharmacy*, 20<sup>th</sup> Edition, Lippincott Williams & White, Baltimore, Md. (2000); and H. C. Ansel et al., *Pharmaceutical Dosage Forms and Drug Delivery Systems*, 7<sup>th</sup> Edition, Lippincott Williams & White, Baltimore, Md. (1999).

Representative examples of materials which can serve as pharmaceutically acceptable carriers include, but are not limited to, the following: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; (21) compressed propellant gases, such as chlorofluorocarbons and hydrofluorocarbons; and (22) other non-toxic compatible substances employed in pharmaceutical compositions.

The pharmaceutical compositions of this invention are typically prepared by thoroughly and intimately mixing or blending a compound of the invention with a pharmaceutically acceptable carrier and one or more optional ingredients. If necessary or desired, the resulting uniformly blended mixture can then be shaped or loaded into tablets, capsules, pills, canisters, cartridges, dispensers and the like using conventional procedures and equipment.

In one embodiment, the pharmaceutical compositions of this invention are suitable for inhaled administration. Suitable pharmaceutical compositions for inhaled administration will typically be in the form of an aerosol or a powder. Such compositions are generally administered using well-known delivery devices, such as a nebulizer inhaler, a metered-dose inhaler (MDI), a dry powder inhaler (DPI) or a similar delivery device.

In a specific embodiment of this invention, the pharmaceutical composition comprising the active agent is administered by inhalation using a nebulizer inhaler. Such nebulizer devices typically produce a stream of high velocity air that causes the pharmaceutical composition comprising the active agent to spray as a mist that is carried into the patient's respiratory tract. Accordingly, when formulated for use in a nebulizer inhaler, the active agent is typically dissolved in a suitable carrier to form a solution. Alternatively, the active agent can be micronized and combined with a suitable carrier to form a suspension of micronized particles of respirable size, where micronized is typically defined as having about 90% or more of the particles with a diameter of less than about 10 µm. Suitable nebulizer devices are provided commercially, for example, by PARI GmbH (Stamberg, German). Other nebulizer devices include Respimat (Boehringer Ingelheim) and those disclosed, for example, in U.S. Pat. No. 6,123,068 to Lloyd et al. and WO 97/12687 (Eicher et al.).

A representative pharmaceutical composition for use in a nebulizer inhaler comprises an isotonic aqueous solution comprising from about 0.05 µg/mL to about 10 mg/mL of a compound of formula I or a pharmaceutically acceptable salt or solvate or stereoisomer thereof.

In another specific embodiment of this invention, the pharmaceutical composition comprising the active agent is administered by inhalation using a dry powder inhaler. Such dry powder inhalers typically administer the active agent as a free-flowing powder that is dispersed in a patient's airstream during inspiration. In order to achieve a free flowing powder, the active agent is typically formulated with a suitable excipient such as lactose or starch.

A representative pharmaceutical composition for use in a dry powder inhaler comprises dry lactose having a particle size between about 1 μm and about 100 μm and micronized particles of a compound of formula I, or a pharmaceutically acceptable salt or solvate or stereoisomer thereof.

Such a dry powder formulation can be made, for example, by combining the lactose with the active agent and then dry blending the components. Alternatively, if desired, the active agent can be formulated without an excipient. The pharmaceutical composition is then typically loaded into a dry powder dispenser, or into inhalation cartridges or capsules for use with a dry powder delivery device.

Examples of dry powder inhaler delivery devices include Diskhaler (GlaxoSmithKline, Research Triangle Park, N.C.) (see, e.g., U.S. Pat. No. 5,035,237 to Newell et al.); Diskus (GlaxoSmithKline) (see, e.g., U.S. Pat. No. 6,378,519 to Davies et al.); Turbuhaler (AstraZeneca, Wilmington, Del.) (see, e.g., U.S. Pat. No. 4,524,769 to Wetterlin); Rotahaler (GlaxoSmithKline) (see, e.g., U.S. Pat. No. 4,353,365 to Hallworth et al.) and Handihaler (Boehringer Ingelheim). Further examples of suitable DPI devices are described in U.S. Pat. No. 5,415,162 to Casper et al., U.S. Pat. No. 5,239,993 to Evans, and U.S. Pat. No. 5,715,810 to Armstrong et al., and references cited therein.

In yet another specific embodiment of this invention, the pharmaceutical composition comprising the active agent is administered by inhalation using a metered-dose inhaler. Such metered-dose inhalers typically discharge a measured amount of the active agent or a pharmaceutically acceptable salt or solvate or stereoisomer thereof using compressed propellant gas. Accordingly, pharmaceutical compositions administered using a metered-dose inhaler typically comprise a solution or suspension of the active agent in a liquefied propellant. Any suitable liquefied propellant may be employed including chlorofluorocarbons, such as $CCl_3F$, and hydrofluoroalkanes (HFAs), such as 1,1,1,2-tetrafluoro-ethane (HFA 134a) and 1,1,1,2,3,3,3-heptafluoro-n-propane, (HFA 227). Due to concerns about chlorofluorocarbons affecting the ozone layer, formulations containing HFAs are generally preferred. Additional optional components of HFA formulations include co-solvents, such as ethanol or pentane, and surfactants, such as sorbitan trioleate, oleic acid, lecithin, and glycerin. See, for example, U.S. Pat. No. 5,225,183 to Purewal et al., EP 0717987 A2 (Minnesota Mining and Manufacturing Company), and WO 92/22286 (Minnesota Mining and Manufacturing Company).

A representative pharmaceutical composition for use in a metered-dose inhaler comprises from about 0.01% to about 5% by weight of a compound of formula I, or a pharmaceutically acceptable salt or solvate or stereoisomer thereof; from about 0% to about 20% by weight ethanol; and from about 0% to about 5% by weight surfactant; with the remainder being an HFA propellant.

Such compositions are typically prepared by adding chilled or pressurized hydrofluoroalkane to a suitable container containing the active agent, ethanol (if present) and the surfactant (if present). To prepare a suspension, the active agent is micronized and then combined with the propellant. The formulation is then loaded into an aerosol canister, which forms a portion of a metered-dose inhaler device. Examples of metered-dose inhaler devices developed specifically for use with HFA propellants are provided in U.S. Pat. No. 6,006,745 to Marecki and U.S. Pat. No. 6,143,277 to Ashurst et al. Alternatively, a suspension formulation can be prepared by spray drying a coating of surfactant on micronized particles of the active agent. See, for example, WO 99/53901 (Glaxo Group Ltd.) and WO 00/61108 (Glaxo Group Ltd.).

For additional examples of processes of preparing respirable particles, and formulations and devices suitable for inhalation dosing see U.S. Pat. Nos. 6,268,533 to Gao et al., U.S. Pat. No. 5,983,956 to Trofast, U.S. Pat. No. 5,874,063 to Briggner et al., and U.S. Pat. No. 6,221,398 to Jakupovic et al.; and WO 99/55319 (Glaxo Group Ltd.) and WO 00/30614 (AstraZeneca AB).

In another embodiment, the pharmaceutical compositions of this invention are suitable for oral administration. Suitable pharmaceutical compositions for oral administration may be in the form of capsules, tablets, pills, lozenges, cachets, dragees, powders, granules; or as a solution or a suspension in an aqueous or non-aqueous liquid; or as an oil-in-water or water-in-oil liquid emulsion; or as an elixir or syrup; and the like; each containing a predetermined amount of a compound of the present invention as an active ingredient.

When intended for oral administration in a solid dosage form (i.e., as capsules, tablets, pills and the like), the pharmaceutical compositions of this invention will typically comprise a compound of the present invention as the active ingredient and one or more pharmaceutically acceptable carriers, such as sodium citrate or dicalcium phosphate. Optionally or alternatively, such solid dosage forms may also comprise: (1) fillers or extenders, such as starches, lactose, sucrose, glucose, mannitol, and/or silicic acid; (2) binders, such as carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and/or sodium carbonate; (5) solution retarding agents, such as paraffin; (6) absorption accelerators, such as quaternary ammonium compounds; (7) wetting agents, such as cetyl alcohol and/or glycerol monostearate; (8) absorbents, such as kaolin and/or bentonite clay; (9) lubricants, such as talc, calcium stearate, magnesium stearate, solid polyethylene glycols, sodium lauryl sulfate, and/or mixtures thereof; (10) coloring agents; and (11) buffering agents.

Release agents, wetting agents, coating agents, sweetening, flavoring and perfuming agents, preservatives and antioxidants can also be present in the pharmaceutical compositions of this invention. Examples of pharmaceutically acceptable antioxidants include: (1) water-soluble antioxidants, such as ascorbic acid, cysteine hydrochloride, sodium bisulfate, sodium metabisulfate sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like. Coating agents for tablets, capsules, pills and like, include those used for enteric coatings, such as cellulose acetate phthalate (CAP), polyvinyl acetate phthalate (PVAP), hydroxypropyl methylcellulose phthalate, methacrylic acid-methacrylic acid ester copolymers, cellulose acetate trimellitate (CAT), carboxymethyl ethyl cellulose (CMEC), hydroxypropyl methyl cellulose acetate succinate (HPMCAS), and the like.

If desired, the pharmaceutical compositions of the present invention may also be formulated to provide slow or controlled release of the active ingredient using, by way of example, hydroxypropyl methyl cellulose in varying proportions; or other polymer matrices, liposomes and/or microspheres.

In addition, the pharmaceutical compositions of the present invention may optionally contain opacifying agents and may be formulated so that they release the active ingredient only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Suitable liquid dosage forms for oral administration include, by way of illustration, pharmaceutically acceptable emulsions, microemulsions, solutions, suspensions, syrups and elixirs. Such liquid dosage forms typically comprise the active ingredient and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (e.g., cottonseed, groundnut, corn, germ, olive, castor and sesame oils), glycerol, tetrahydrofuryl alcohol, polyethylene glycols and fatty acid esters of sorbitan, and mixtures thereof. Suspensions, in addition to the active ingredient, may contain suspending agents such as, for example, ethoxylated isostearyl alcohols, polyoxyethylene sorbitol and sorbitan esters, microcrystalline cellulose, aluminium metahydroxide, bentonite, agar-agar and tragacanth, and mixtures thereof.

When intended for oral administration, the pharmaceutical compositions of this invention are preferably packaged in a unit dosage form. The term "unit dosage form" means a physically discrete unit suitable for dosing a patient, i.e., each unit containing a predetermined quantity of active agent calculated to produce the desired therapeutic effect either alone or in combination with one or more additional units. For example, such unit dosage forms may be capsules, tablets, pills, and the like.

The compounds of this invention can also be administered transdermally using known transdermal delivery systems and excipients. For example, a compound of this invention can be admixed with permeation enhancers, such as propylene glycol, polyethylene glycol monolaurate, azacycloalkan-2-ones and the like, and incorporated into a patch or similar delivery system. Additional excipients including gelling agents, emulsifiers and buffers, may be used in such transdermal compositions if desired.

The pharmaceutical compositions of this invention may also contain other therapeutic agents that are co-administered with a compound of formula I, or pharmaceutically acceptable salt or solvate or stereoisomer thereof. For example, the pharmaceutical compositions of this invention may further comprise one or more therapeutic agents selected from other bronchodilators (e.g., $PDE_3$ inhibitors, adenosine 2b modulators and $\beta_2$ adrenergic receptor agonists); anti-inflammatory agents (e.g., steroidal anti-inflammatory agents, such as corticosteroids; non-steroidal anti-inflammatory agents (NSAIDs), and $PDE_4$ inhibitors); other muscarinic receptor antagonists (i.e., antichlolinergic agents); antiinfective agents (e.g., Gram positive and Gram negative antibiotics or antivirals); antihistamines; protease inhibitors; and afferent blockers (e.g., $D_2$ agonists and neurokinin modulators). In one particular aspect of the invention, the compound of the invention is co-administered with a $\beta_2$ adrenergic receptor agonist and a steroidal anti-inflammatory agent. The other therapeutic agents can be used in the form of pharmaceutically acceptable salts or solvates. Additionally, if appropriate, the other therapeutic agents can be used as optically pure stereoisomers.

Representative $\beta_2$ adrenergic receptor agonists that can be used in combination with the compounds of this invention include, but are not limited to, salmeterol, salbutamol, formoterol, salmefamol, fenoterol, terbutaline, albuterol, isoetharine, metaproterenol, bitolterol, pirbuterol, levalbuterol and the like, or pharmaceutically acceptable salts thereof. Other $\beta_2$ adrenergic receptor agonists that can be used in combination with the compounds of this invention include, but are not limited to, 3-(4-{[6-({(2R)-2-hydroxy-2-[4-hydroxy-3-(hydroxymethyl)-phenyl]ethyl}amino)-hexyl]oxy}butyl)benzenesulfonamide and 3-(-3-{[7-({(2R)-2-hydroxy-2-[4-hydroxy-3-(hydroxymethyl)phenyl]ethyl}-amino)heptyl]oxy}-propyl)benzenesulfonamide and related compounds disclosed in WO 02/066422 (Glaxo Group Ltd.); 3-[3-(4-{[6-([(2R)-2-hydroxy-2-[4-hydroxy-3-(hydroxymethyl)phenyl]ethyl}amino)hexyl]oxy}butyl)-phenyl]imidazolidine-2,4-dione and related compounds disclosed in WO 02/070490 (Glaxo Group Ltd.); 3-(4-{[6-({(2R)-2-[3-(formylamino)-4-hydroxyphenyl]-2-hydroxyethyl}amino)hexyl]oxy}butyl)-benzenesulfonamide, 3-(4-{[6-({(2S)-2-[3-(formylamino)-4-hydroxyphenyl]-2-hydroxyethyl}amino)hexyl]oxy}butyl)-benzenesulfonamide, 3-(4-{[6-({(2R/S)-2-[3-(formylamino)-4-hydroxyphenyl]-2-hydroxyethyl}amino)hexyl]oxy}butyl)-benzenesulfonamide, N-(tert-butyl)-3-(4-{[6-({(2R)-2-[3-(formylamino)-4-hydroxyphenyl]-2-hydroxyethyl}amino)hexyl]-oxy}butyl) benzenesulfonamide, N-(tert-butyl)-3-(4-{[6-({(2S)-2-[3-(formylamino)-4-hydroxyphenyl]-2-hydroxyethyl}amino)hexyl]oxy}butyl)-benzenesulfonamide, N-(tert-butyl)-3-(4-{[6-({(2R/S)-2-[3-(formylamino)-4-hydroxyphenyl]-2-hydroxyethyl}amino)hexyl]-oxy}butyl) benzenesulfonamide and related compounds disclosed in WO 02/076933 (Glaxo Group Ltd.); 4-{(1R)-2-[(6-{2-[(2,6-dichlorobenzyl)oxy]ethoxy}hexyl)amino]-1-hydroxyethyl}-2-(hydroxymethyl)phenol and related compounds disclosed in WO 03/024439 (Glaxo Group Ltd.); N-{2-[4-((R)-2-hydroxy-2-phenylethylamino)phenyl]ethyl}-(R)-2-hydroxy-2-(3-formamido-4-hydroxyphenyl)ethylamine and related compounds disclosed in U.S. Pat. No. 6,576,793 to Moran et al.; N-{2-[4-(3-phenyl-4-methoxyphenyl)aminophenyl]ethyl}-(R)-2-hydroxy-2-(8-hydroxy-2(1H)-quinolinon-5-yl)ethylamine and related compounds disclosed in U.S. Pat. No. 6,653,323 to Moran et al.; and pharmaceutically acceptable salts thereof. In a particular embodiment, the $\beta_2$-adrenoreceptor agonist is a crystalline monohydrochloride salt of N-{2-[4-((R)-2-hydroxy-2-phenylethylamino)phenyl]ethyl}-(R)-2-hydroxy-2-(3-formamido-4-hydroxyphenyl)ethylamine. When employed, the $\beta_2$-adrenoreceptor agonist will be present in the pharmaceutical composition in a therapeutically effective amount. Typically, the $\beta_2$-adrenoreceptor agonist will be present in an amount sufficient to provide from about 0.05 µg to about 500 µg per dose.

Representative steroidal anti-inflammatory agents that can be used in combination with the compounds of this invention include, but are not limited to, methyl prednisolone, prednisolone, dexamethasone, fluticasone propionate, 6α,9α-difluoro-17α-[(2-furanylcarbonyl)oxy]-11β-hydroxy-16α-methyl-3-oxoandrosta-1,4-diene-17β-carbothioic acid S-fluoromethyl ester, 6α,9α-difluoro-11β-hydroxy-16α-methyl-3-oxo-17α-propionyloxy-androsta-1,4-diene-17β-carbothioic acid S-(2-oxo-tetrahydrofuran-3S-yl) ester, beclomethasone esters (e.g., the 17-propionate ester or the 17,21-dipropionate ester), budesonide, flunisolide, mometasone esters (e.g., the furoate ester), triamcinolone acetonide, rofleponide, ciclesonide, butixocort propionate, RPR-106541, ST-126 and the like, or pharmaceutically-acceptable salts thereof. When employed, the steroidal anti-inflammatory agent will be present in the pharmaceutical composition in a therapeutically effective amount. Typically, the steroidal anti-inflammatory agent will be present in an amount sufficient to provide from about 0.05 µg to about 500 µg per dose.

An exemplary combination is a compound of formula I, or pharmaceutically acceptable salt or solvate or stereoisomer thereof, co-administered with salmeterol as the $\beta_2$ adrenergic receptor agonist, and fluticasone propionate as the steroidal anti-inflammatory agent. Another exemplary combination is a compound of formula I, or pharmaceutically acceptable salt or solvate or stereoisomer thereof, co-administered with a crystalline monohydrochloride salt of N-{2-[4-((R)-2-hydroxy-2-phenylethylamino)phenyl]ethyl}-(R)-2-hydroxy-2-(3-formamido-4-hydroxyphenyl)ethylamine as the $\beta_2$-adrenoreceptor agonist, and 6α,9α-difluoro-17α-[(2-furanylcarbonyl)oxy]-11β-hydroxy-16α-methyl-3-oxoandrosta-1,4-diene-17β-carbothioic acid S-fluoromethyl ester as the steroidal anti-inflammatory agent.

Other suitable combinations include, for example, other anti-inflammatory agents, e.g., NSAIDs (such as sodium cromoglycate; nedocromil sodium; phosphodiesterase (PDE) inhibitors (e.g., theophylline, PDE4 inhibitors or mixed PDE3/PDE4 inhibitors); leukotriene antagonists (e.g., monteleukast); inhibitors of leukotriene synthesis; iNOS inhibitors; protease inhibitors, such as tryptase and elastase inhibitors; beta-2 integrin antagonists and adenosine receptor agonists or antagonists (e.g., adenosine 2a agonists); cytokine antagonists (e.g., chemokine antagonists such as, an interleukin antibody (αIL antibody), specifically, an αIL-4 therapy, an αIL-13 therapy, or a combination thereof); or inhibitors of cytokine synthesis.

For example, representative phosphodiesterase-4 (PDE4) inhibitors or mixed PDE3/PDE4 inhibitors that can be used in combination with the compounds of this invention include, but are not limited to cis 4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one; cis-[4-cyano-4-(3-cyclopropylmethoxy-4-difluoromethoxyphenyl)cyclohexan-1-ol]; cis-4-cyano-4-[3-(cyclopentyloxy)-4-methoxyphenyl]cyclohexane-1-carboxylic acid and the like, or pharmaceutically acceptable salts thereof. Other representative PDE4 or mixed PDE4/PDE3 inhibitors include AWD-12-281 (elbion); NCS-613 (INSERM); D-4418 (Chiroscience and Schering-Plough); CI-1018 or PD-168787 (Pfizer); benzodioxole compounds disclosed in WO99/16766 (Kyowa Hakko); K-34 (Kyowa Hakko); V-11294A (Napp); roflumilast (Byk-Gulden); pthalazinone compounds disclosed in WO99/47505 (Byk-Gulden); Pumafentrine (Byk-Gulden, now Altana); arofylline (Almirall-Prodesfarma); VM554/UM565 (Vemalis); T-440 (Tanabe Seiyaku); and T2585 (Tanabe Seiyaku).

Representative muscarinic antagonists (i.e., anticholinergic agents) that can be used in combination with, and in addition to, the compounds of this invention include, but are not limited to, atropine, atropine sulfate, atropine oxide, methylatropine nitrate, homatropine hydrobromide, hyoscyamine (d, l) hydrobromide, scopolamine hydrobromide, ipratropium bromide, oxitropium bromide, tiotropium bromide, methantheline, propantheline bromide, anisotropine methyl bromide, clidinium bromide, copyrrolate (Robinul), isopropamide iodide, mepenzolate bromide, tridihexethyl chloride (Pathilone), hexocyclium methylsulfate, cyclopentolate hydrochloride, tropicamide, trihexyphenidyl hydrochloride, pirenzepine, telenzepine, AF-DX 116 and methoctramine and the like, or a pharmaceutically acceptable salt thereof; or, for those compounds listed as a salt, alternate pharmaceutically acceptable salt thereof.

Representative antihistamines (i.e., $H_1$-receptor antagonists) that can be used in combination with the compounds of this invention include, but are not limited to, ethanolamines, such as carbinoxamine maleate, clemastine fumarate, diphenylhydramine hydrochloride and dimenhydrinate; ethylenediamines, such as pyrilamine amleate, tripelennamine hydrochloride and tripelennamine citrate; alkylamines, such as chlorpheniramine and acrivastine; piperazines, such as hydroxyzine hydrochloride, hydroxyzine pamoate, cyclizine hydrochloride, cyclizine lactate, meclizine hydrochloride and cetirizine hydrochloride; piperidines, such as astemizole, levocabastine hydrochloride, loratadine or its descarboethoxy analogue, terfenadine and fexofenadine hydrochloride; azelastine hydrochloride; and the like, or a pharmaceutically acceptable salt thereof; or, for those compounds listed as a salt, alternate pharmaceutically acceptable salt thereof.

Suitable doses for the other therapeutic agents administered in combination with a compound of the invention are in the range of about 0.05 µg/day to about 100 mg/day.

The following formulations illustrate representative pharmaceutical compositions of the present invention:

Formulation Example A

A dry powder for administration by inhalation is prepared as follows:

| Ingredients | Amount |
| --- | --- |
| Compound of the invention | 0.2 mg |
| Lactose | 25 mg |

Representative Procedure: The compound of the invention is micronized and then blended with lactose. This blended mixture is then loaded into a gelatin inhalation cartridge. The contents of the cartridge are administered using a powder inhaler.

Formulation Example B

A dry powder formulation for use in a dry powder inhalation device is prepared as follows:

Representative Procedure: A pharmaceutical composition is prepared having a bulk formulation ratio of micronized compound of the invention to lactose of 1:200. The composition is packed into a dry powder inhalation device capable of delivering between about 10 µg and about 100 µg of the compound of the invention per dose.

Formulation Example C

A dry powder for administration by inhalation in a metered dose inhaler is prepared as follows:

Representative Procedure: A suspension containing 5 wt % of a compound of the invention and 0.1 wt % lecithin is prepared by dispersing 10 g of the compound of the invention as micronized particles with mean size less than 10 µm in a solution formed from 0.2 g of lecithin dissolved in 200 mL of demineralized water. The suspension is spray dried and the resulting material is micronized to particles having a mean diameter less than 1.5 μm. The particles are loaded into cartridges with pressurized 1,1,1,2-tetrafluoroethane.

Formulation Example D

A pharmaceutical composition for use in a metered dose inhaler is prepared as follows:

Representative Procedure: A suspension containing 5 wt % compound of the invention, 0.5 wt % lecithin, and 0.5 wt % trehalose is prepared by dispersing 5 g of active ingredient as micronized particles with mean size less than 10 μm in a colloidal solution formed from 0.5 g of trehalose and 0.5 g of lecithin dissolved in 100 mL of demineralized water. The suspension is spray dried and the resulting material is micronized to particles having a mean diameter less than 1.5 μm. The particles are loaded into canisters with pressurized 1,1,1,2-tetrafluoroethane.

Formulation Example E

A pharmaceutical composition for use in a nebulizer inhaler is prepared as follows:

Representative Procedure: An aqueous aerosol formulation for use in a nebulizer is prepared by dissolving 0.1 mg of the compound of the invention in 1 mL of a 0.9% NaCl solution acidified with citric acid. The mixture is stirred and sonicated until the active ingredient is dissolved. The pH of the solution is adjusted to a value in the range of from 3 to 8 by the slow addition of NaOH.

Formulation Example F

Hard gelatin capsules for oral administration are prepared as follows:

| Ingredients | Amount |
| --- | --- |
| Compound of the invention | 250 mg |
| Lactose (spray-dried) | 200 mg |
| Magnesium stearate | 10 mg |

Representative Procedure: The ingredients are thoroughly blended and then loaded into a hard gelatin capsule (460 mg of composition per capsule).

Formulation Example G

A suspension for oral administration is prepared as follows:

| Ingredients | Amount |
| --- | --- |
| Compound of the invention | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum k (Vanderbilt Co.) | 1.0 g |
| Flavoring | 0.035 mL |
| Colorings | 0.5 mg |
| Distilled water | q.s. to 100 mL |

Representative Procedure: The ingredients are mixed to form a suspension containing 100 mg of active ingredient per 10 mL of suspension.

Formulation Example H

An injectable formulation is prepared as follows:

| Ingredients | Amount |
| --- | --- |
| Compound of the invention | 0.2 g |
| Sodium acetate buffer solution (0.4 M) | 2.0 mL |
| HCl (0.5 N) or NaOH (0.5 N) | q.s. to pH 4 |
| Water (distilled, sterile) | q.s. to 20 mL |

Representative Procedure: The above ingredients are blended and the pH is adjusted to 4±0.5 using 0.5 N HCl or 0.5 N NaOH.

Utility

The diphenylmethyl compounds of this invention are expected to be useful as muscarinic receptor antagonists and therefore, such compounds are expected to be useful for treating medical conditions mediated by muscarinic receptors, i.e., medical conditions which are ameliorated by treatment with a muscarinic receptor antagonist. Such medical conditions include, by way of example, pulmonary disorders or diseases including those associated with reversible airway obstruction, such as chronic obstructive pulmonary disease (e.g., chronic and wheezy bronchitis and emphysema), asthma, pulmonary fibrosis, allergic rhinitis, rhinorrhea, and the like. Other medical conditions that can be treated with muscarinic receptor antagonists are genitourinary tract disorders, such as overactive bladder or detrusor hyperactivity and their symptoms; gastrointestinal tract disorders, such as irritable bowel syndrome, diverticular disease, achalasia, gastrointestinal hypermotility disorders and diarrhea; cardiac arrhythmias, such as sinus bradycardia; Parkinson's disease; cognitive disorders, such as Alzheimer's disease; dismenorrhea; and the like.

In one embodiment, the compounds of this invention are useful for treating smooth muscle disorders in mammals, including humans and their companion animals (e.g., dogs, cats etc.). Such smooth muscle disorders include, by way of illustration, overactive bladder, chronic obstructive pulmonary disease and irritable bowel syndrome.

When used to treat smooth muscle disorders or other conditions mediated by muscarinic receptors, the compounds of this invention will typically be administered orally, rectally, parenterally or by inhalation in a single daily dose or in multiple doses per day. The amount of active agent administered per dose or the total amount administered per day will typically be determined by the patient's physician and will depend on such factors as the nature and severity of the patients condition, the condition being treated, the age and general health of the patient, the tolerance of the patient to the active agent, the route of administration and the like.

Typically, suitable doses for treating smooth muscle disorders or other disorders mediated by muscarinic receptors will range from about 0.14 μg/kg/day to about 7 mg/kg/day of active agent; including from about 0.15 μg/kg/day to about 5 mg/kg/day. For an average 70 kg human, this would amount to about 10 μg per day to about 500 mg per day of active agent.

In a specific embodiment, the compounds of this invention are useful for treating pulmonary or respiratory disorders, such as COPD or asthma, in mammals including humans. When used to treat such disorders, the compounds of this invention will typically be administered by inhalation in multiple doses per day, in a single daily dose or a single weekly dose. Generally, the dose for treating a pulmonary disorder will range from about 10 μg/day to about 200 μg/day. As used herein, COPD includes chronic obstructive bronchitis and emphysema (see, for example, Barnes, Chronic Obstructive Pulmonary Disease, *N Engl J Med* 343:269-78 (2000)).

When used to treat a pulmonary disorder, the compounds of this invention are optionally administered in combination with other therapeutic agents such as a $\beta_2$-adrenoreceptor agonist; a corticosteroid, a non-steroidal anti-inflammatory agent, or combinations thereof.

When administered by inhalation, the compounds of this invention typically have the effect of producing bronchodilation. Accordingly, in another of its method aspects, this invention is directed to a method of producing bronchodilation in a patient, the method comprising administering to a patient a bronchodilation-producing amount of a compound of the invention. Generally, the therapeutically effective dose for producing bronchodilation will range from about 10 μg/day to about 200 μg/day.

In another embodiment, the compounds of this invention are used to treat overactive bladder. When used to treat overactive bladder, the compounds of this invention will typically be administered orally in a single daily dose or in multiple doses per day; preferably in a single daily dose. Preferably, the dose for treating overactive bladder will range from about 1.0 to about 500 mg/day.

In yet another embodiment, the compounds of this invention are used to treat irritable bowel syndrome. When used to treat irritable bowel syndrome, the compounds of this invention will typically be administered orally or rectally in a single daily dose or in multiple doses per day. Preferably, the dose for treating irritable bowel syndrome will range from about 1.0 to about 500 mg/day.

Since compounds of this invention are muscarinic receptor antagonists, such compounds are also useful as research tools for investigating or studying biological systems or samples having muscarinic receptors. Such biological systems or samples may comprise $M_1$, $M_2$, $M_3$, $M_4$ and/or $M_5$ muscarinic receptors. Any suitable biological system or sample having muscarinic receptors may be employed in such studies which may be conducted either in vitro or in vivo. Representative biological systems or samples suitable for such studies include, but are not limited to, cells, cellular extracts, plasma membranes, tissue samples, mammals (such as mice, rats, guinea pigs, rabbits, dogs, pigs, etc.), and the like.

In this embodiment, a biological system or sample comprising a muscarinic receptor is contacted with a muscarinic receptor-antagonizing amount of a compound of this invention. The effects of antagonizing the muscarinic receptor are then determined using conventional procedures and equipment, such as radioligand binding assays and functional assays. Such functional assays include ligand-mediated changes in intracellular cyclic adenosine monophosphate (cAMP), ligand-mediated changes in activity of the enzyme adenylyl cyclase (which synthesizes cAMP), ligand-mediated changes in incorporation of guanosine 5'-O-(γ-thio)triphosphate ([$^{35}$S]GTPγS) into isolated membranes via receptor catalyzed exchange of [$^{35}$S]GTPγS for GDP, ligand-mediated changes in free intracellular calcium ions (measured, for example, with a fluorescence-linked imaging plate reader or FLIPR® from Molecular Devices, Inc.). A compound of this invention will antagonize or decrease the activation of muscarinic receptors in any of the functional assays listed above, or assays of a similar nature. A muscarinic receptor-antagonizing amount of a compound of this invention will typically range from about 0.1 nanomolar to about 100 nanomolar.

Additionally, the compounds of this invention can be used as research tools for discovering new compounds that have muscarinic receptor antagonist activity. In this embodiment, muscarinic receptor binding data (e.g., as determined by in vitro radioligand displacement assays) for a test compound or a group of test compounds is compared to the muscarinic receptor binding data for a compound of this invention to identify those test compounds that have about equal or superior muscarinic receptor binding, if any. This aspect of the invention includes, as separate embodiments, both the generation of comparison data (using the appropriate assays) and the analysis of the test data to identify test compounds of interest.

In another embodiment, the compounds of this invention are used to antagonize a muscarinic receptor in biological system, and a mammal in particular, such as mice, rats, guinea pigs, rabbits, dogs, pigs, humans and so forth. In this embodiment, a therapeutically effective amount of the compound of formula I is administered to the mammal. The effects of antagonizing the muscarinic receptor can then determined using conventional procedures and equipment, examples of which are described above.

Among other properties, compounds of this invention have been found to be potent inhibitors of $M_3$ muscarinic receptor activity. Accordingly, in a specific embodiment, this invention is directed to compounds of formula I having an inhibition dissociation constant ($K_i$) for the $M_3$ receptor subtype of less than or equal to 100 nM; preferably, less than or equal to 50 nM; and more preferably, less than or equal to 10 nM (as determined, for example, by an in vitro radioligand displacement assay).

Additionally, compounds of this invention are expected to possess a desirable duration of action. Accordingly, in another specific embodiment, this invention is directed to compounds of formula I having a duration of action greater than about 24 hours.

Moreover, compounds of this invention are also expected to possess reduced side effects, such as dry mouth, at efficacious doses when administered by inhalation compared to other known muscarinic receptor antagonists administered by inhalation (such as tiotropium).

These properties, as well as the utility of the compounds of this invention, can be demonstrated using various in vitro and in vivo assays well-known to those skilled in the art. For example, representative assays are described in further detail in the following Examples.

EXAMPLES

The following Preparations and Examples illustrate specific embodiments of this invention. In these examples, the following abbreviations have the following meanings:

| | |
|---|---|
| AC | adenylyl cyclase |
| ACh | acetylcholine |
| ACN | acetonitrile |
| BSA | bovine serum albumin |

-continued

| | |
|---|---|
| cAMP | 3'-5' cyclic adenosine monophosphate |
| CHO | Chinese hamster ovary |
| $cM_5$ | cloned chimpanzee $M_5$ receptor |
| DABCO | 1,4-diazabicyclo[2.2.2]octane |
| DCM | dichloromethane (i.e., methylene chloride) |
| DIBAL | diisobutylaluminum hydride |
| DIPEA | N,N-diisopropylethylamine |
| dPBS | Dulbecco's phosphate buffered saline |
| DMF | dimethylformamide |
| DMSO | dimethyl sulfoxide |
| EDTA | ethylenediamine tetraacetic acid |
| EtOAc | ethyl acetate |
| EtOH | ethanol |
| FBS | fetal bovine serum |
| FLIPR | fluorometric imaging plate reader |
| HATU | O-(7-azabenzotriazol-1-yl-N,N,N',N'-tetramethyluronium hexafluorophosphate |
| HEPES | 4-(2-hydroxyethyl)-1-piperazineethanesulfonic acid |
| $hM_1$ | cloned human $M_1$ receptor |
| $hM_2$ | cloned human $M_2$ receptor |
| $hM_3$ | cloned human $M_3$ receptor |
| $hM_4$ | cloned human $M_4$ receptor |
| $hM_5$ | cloned human $M_5$ receptor |
| HPLC | high-performance liquid chromatography |
| IPAc | isopropyl acetate |
| MCh | methylcholine |
| MeOH | methanol |
| MTBE | methyl tert-butyl ether |
| PyBOP | benzotriazol-1-yloxytripyrrolidinophosphonium hexafluorophosphate |
| TFA | trifluoroacetic acid |
| THF | tetrahydrofuran |

Any other abbreviations used herein but not defined have their standard, generally accepted meaning. Unless noted otherwise, all materials, such as reagents, starting materials and solvents, were purchased from commercial suppliers (such as Sigma-Aldrich, Fluka, and the like) and were used without further purification.

Unless otherwise indicated, HPLC analysis was conducted using an Agilent (Palo Alto, Calif.) Series 1100 instrument equipped with a Zorbax Bonus RP 2.1×50 mm column (Agilent) having a 3.5 micron particle size. Detection was by UV absorbance at 214 nm. The mobile phases employed were as follows (by volume): A is ACN (2%), water (98%) and TFA (0.1%); and B is ACN (90%), water (10%) and TFA (0.1%). HPLC 10-70 data was obtained using a flow rate of 0.5 mL/minute of 10 to 70% B over a 6 minute gradient (with the remainder being A). Similarly, HPLC 5-35 data and HPLC 10-90 data were obtained using 5 to 35% B; or 10 to 90% B over a 5 minute gradient.

Liquid chromatography mass spectrometry (LCMS) data were obtained with an Applied Biosystems (Foster City, Calif.) Model API-150EX instrument. LCMS 10-90 data was obtained using 10 to 90% Mobile Phase B over a 5 minute gradient.

Small-scale purification was conducted using an API 150EX Prep Workstation system from Applied Biosystems. The mobile phases employed were as follows (by volume): A is water and 0.05% TFA; and B is ACN and 0.05% TFA. For arrays (typically about 3 to 50 mg recovered sample size) the following conditions were used: 20 mL/min flow rate; 15 min gradients and a 20 mm×50 mm Prism RP column with 5 micron particles (Thermo Hypersil-Keystone, Bellefonte, Pa.). For larger scale purifications (typically greater than 100 mg crude sample), the following conditions were used: 60 mL/min flow rate; 30 min gradients and a 41.4 mm×250 mm Microsorb BDS column with 10 micron particles (Varian, Palo Alto, Calif.).

Example A

Preparation of 2,2-Diphenyl-2-(S)-pyrrolidin-3-ylacetamide

Step A: Preparation of (S)-1-Benzyl-3-(p-toluenesulfonyloxy)pyrrolidine

To a stirred solution of (S)-1-benzyl-3-pyrrolidinol (44.3 g, 0.25 mol) and 1,4-diazabicyclo[2.2.2]octane (33.7 g, 0.3 mol) in 250 mL of tert-butyl methyl ether under an atmosphere of nitrogen at 0° C., was added p-toluenesulfonyl chloride (52.4 g, 0.275 mol) portion-wise over 20 minutes. The reaction mixture was stirred at 0° C. for 1 hour. The ice bath was removed and the mixture was stirred at ambient temperature overnight (20±5 h). EtOAc (100 mL) was added, followed by saturated aqueous sodium bicarbonate solution (250 mL). The resulting mixture was stirred at ambient temperature for 1 hour. The layers were separated and the organic layer was washed with saturated aqueous sodium bicarbonate solution (250 mL); saturated aqueous ammonium chloride solution (250 mL); saturated aqueous NaCl solution (250 mL); and then dried over sodium sulfate (80 g). The sodium sulfate was filtered off and washed with ethyl acetate (20 mL) and the solvent was removed in vacuo to give 78.2 g of the title intermediate as an off-white solid (94% yield).

HPLC analysis of this intermediate was conducted using a YMC ODSA C18 4.6×50 mm column, having a 5.0 micron particle size. Detection was by UV absorbance at 220 nm. The mobile phases employed were as follows (by volume): A is MeOH (10%), water (90%) and TFA (0.1%); and B is MeOH (90%), water (10%) and TFA (0.1%). Using a flow rate of 4.0 mL/min of 0 to 100% B in A over 5 minutes, this intermediate was determined to have a purity of 95%.

Step B: Preparation of (S)-1-Benzyl-3-(1-cyano-1,1-diphenylmethyl)-pyrrolidine

To a stirred solution of diphenylacetonitrile (12.18 g, 61.8 mmol) in anhydrous THF (120 mL) at 0° C., potassium tert-butoxide (10.60 g, 94.6 mmol) was added over 5 min. The reaction mixture was stirred at 0° C. for 1 h. To the reaction mixture at 0° C. was added (S)-1-benzyl-3-(p-toluenesulfonyloxy)-pyrrolidine (20.48 g, 61.3 mmol) in one portion. The cold bath was removed and the reaction mixture was stirred for 5-10 min at which time the reaction mixture had become a brown homogeneous solution. The reaction mixture was then heated at 40° C. overnight (20±5 h). The reaction mixture (bright yellow suspension) was allowed to cool to ambient temperature before adding water (150 mL). Most of the THF was then removed in vacuo and IPAc (200 mL) was added. The layers were separated and the organic layer was washed with saturated aqueous ammonium chloride solution (150 mL); saturated aqueous NaCl solution (150 mL); and then dried over sodium sulfate (50 g). The sodium sulfate was filtered off and washed with IPAc (20 mL) and the solvent was removed in vacuo to give 23.88 g of the title intermediate as a light brown oil (>99% yield). This intermediate was determined to have a purity of 75% (contaminated mainly with excess diphenylacetonitriie) using the HPLC method described in Step A.

Step C: Preparation of (S)-3-(1-Cyano-1,1-diphenylmethyl)pyrrolidine (S)-1-Benzyl-3-(1-cyano-1,1-diphenylmethyl)pyrrolidine was dissolved in IPAc (approximately 1 g/10 mL) and the solution was mixed with an equal volume of 1N aqueous HCl. The resulting layers were separated and the aqueous layer was extracted with an equal volume of IPAc. The organic layers were combined, dried over sodium sulfate and filtered. The solvent was removed in vacuo to afford (S)-1-benzyl-3-(1-cyano-1,1-diphenylmethyl)pyrrolidine hydrochloride as a light yellow foamy solid. (Note: This hydrochloride salt can also be prepared during the work-up of Step B).

To a stirred solution of (S)-1-benzyl-3-(1-cyano-1,1-diphenylmethyl)pyrrolidine hydrochloride (8.55 g, 21.98 mmol) in MeOH (44 mL) was added palladium on carbon (1.71 g) and ammonium formate (6.93 g, 109.9 mmol). The reaction mixture was heated to 50° C. with stirring for 3 hours. The reaction was cooled to ambient temperature and water (20 mL) was added. The resulting mixture was filtered through a pad of Celite, washing with MeOH (20 mL). The filtrate was collected and most of the MeOH was removed in vacuo. The residue was mixed with IPAc (100 mL) and 10% aqueous sodium carbonate (50 mL). The resulting layers were separated and the aqueous layer was extracted with IPAc (50 mL). The organic layers were combined and dried over sodium sulfate (20 g). The sodium sulfate was filtered off and washed with IPAc (20 mL). The solvent was removed in vacuo to afford 5.75 g of the title intermediate as a light yellow oil (99.7% yield, 71% purity by HPLC).

Step D: Preparation of 2,2-Diphenyl-2-(S)-pyrrolidin-3-ylacetamide

A 200 mL flask with a magnetic stir bar and a nitrogen inlet was charged with (S)-3-(1-cyano-1,1-diphenylmethyl)pyrrolidine (2.51 g) and 80% $H_2SO_4$ (19.2 mL; pre-prepared with 16 mL of 96% $H_2SO_4$ and 3.2 mL of $H_2O$). The reaction mixture was then heated at 90° C. for 24 hours or until the starting material was consumed as indicated by HPLC. The reaction mixture was allowed to cool to ambient temperature and then poured onto ice (approximately 50 mL by volume). A 50% aqueous NaOH solution was added slowly to the mixture with stirring over an ice bath until the pH was about 12. DCM (200 mL) was added and mixed with the aqueous solution at which time sodium sulfate precipitated out and was filtered off. The filtrate was collected and the layers were separated. The aqueous layer was extracted with DCM (100 mL) and the organic layers were combined and dried with over sodium sulfate (5 g). The sodium sulfate was filtered off and washed with DCM (10 mL). The solvent was removed in vacuo to give the crude product as a light yellow foamy solid (ca. 2.2 g, 86% purity by HPLC).

The crude product was dissolved in EtOH (18 mL) with stirring. To this solution was added a warm solution of L-tartaric acid (1.8 g) in EtOH (14 mL) and the resulting mixture was stirred overnight (15±5 h). The resulting precipitate was isolated by filtration to give an off-white solid (ca. 3.2 g, >95% purity by HPLC). MeOH (15 mL) was added to this solid and the resulting slurry was stirred at 70° C. overnight (15 hours). The slurry was allowed to cool to ambient temperature and a white solid (~2.6 g, >99% purity by HPLC) was obtained after filtration. To this solid was added EtOAc (30 mL) and 1 N aqueous NaOH (25 mL). This mixture was mixed until two distinct layers formed and then the layers were separated and the aqueous layer was extracted with EtOAc (20 mL). The organic layers were combined and dried over sodium sulfate (10 g). The sodium sulfate was removed by filtration and the solvent was evaporated in vacuo to afford 1.55 g of the title intermediate as an off-white foamy solid (58% yield).

HPLC analysis was conducted using an Inertsil OCD-2 C18 column. Detection was by UV absorbance at 254 nm. The mobile phases employed were as follows (by volume): A is MeOH (5%), water (95%), and TFA (0.1%); and B is MeOH (95%), water (5%) and TFA (0.1%). Using a flow rate of 1.0 mL/min of 0 to 100% B in A over 15 minutes, this intermediate was determined to have a purity of >99%.

Example 1

Synthesis of 2-{(S)-1-[4-(4-Aminophenyl)butyl]pyrrolidin-3-yl}-2,2-diphenylacetamide

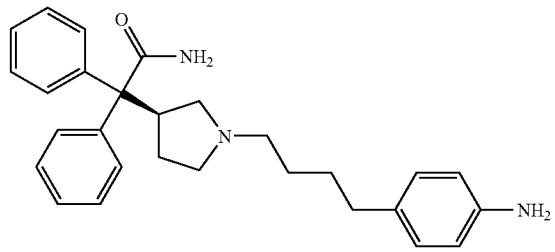

Step A: Preparation of 2-{(S)-1-[4-(4-Aminophenyl)butyryl]pyrrolidin-3-yl}-2,2-diphenylacetamide Diisopropylethylamine (0.809 mL, 4.6 mmol) was added to a solution of 2,2-diphenyl-2-(S)-pyrrolidin-3-ylacetamide (1.00 g, 3.6 mmol) and 4-(4-aminophenyl)butyric acid (0.646 g, 3.61 mmol) in DMF (17 mL) and the resulting mixture was stirred at ambient temperature. After about 15 minutes, HATU (1.63 g, 4.3 mmol) was added and the reaction mixture was stirred for two hours. The reaction mixture was concentrated to one half its volume and then diluted with DCM (15 mL). The layers were separated and the organic layer was washed with saturated aqueous sodium bicarbonate solution (3×15 mL), brine (15 mL), dried over magnesium sulfate, and then concentrated under vacuum. The crude product was purified on a silica gel column using MeOH (5%)/DCM (95%) as the eluent to afford 700 mg of the title intermediate as a solid. MS m/z: [M+H$^+$] calc'd for $C_{28}H_{31}N_3O_3$ 442.2; found 442.3.

Step B: Preparation of 2-{(S)-1-[4-(4-Aminophenyl)butyl]pyrrolidin-3-yl}-2,2-diphenylacetamide ditrifluoroacetate salt A solution of DIBAL in toluene (1M, 1.64 mL) was added to a solution of the intermediate from Step A (0.24 g, 0.54 mmol) in THF (3.6 mL) at ambient temperature and the resulting mixture was stirred for 72 hours. The reaction mixture was then concentrated and the residue was added to a 1:1 mixture of water and ACN (1 mL) containing 0.01% TFA. This mixture was then purified by HPLC to give 37.4 mg of the title compound as the bis(trifluoroacetate) salt. MS m/z: [M+H$^+$] calc'd for $C_{28}H_{33}N_3O$ 428.3; found 428.6.

Example 2

Synthesis of 2-((S)-1-{2-[4-(2-Methylaminoethyl)phenyl]ethyl}pyrrolidin-3-yl)-2,2-diphenyl-acetamide

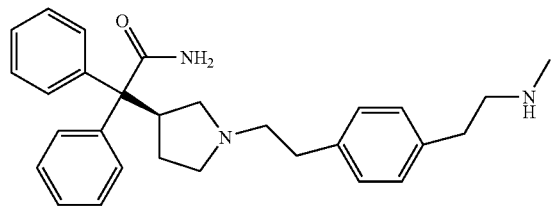

Step A: Preparation {4-[(N-Benzyl-N-methylcarbamoyl)methyl]phenyl}acetic Acid

To a 2-L three-necked flask, equipped with a magnetic stir bar, nitrogen gas inlet and addition funnel, was added 1,4-phenylenediacetic acid (50 g, 257 mmol), PyBOP (127.5 g, 245 mmol) and DCM (700 mL). The reaction mixture was then cooled to 0° C. to 10° C. A solution of benzylmethylamine (34.81 mL, 269.7 mmol) and DIPEA (85.4 mL, 490 mmol) in DCM (300 mL) was then added slowly and the reaction mixture was stirred at ambient temperature overnight (~16 hours). The reaction mixture was then washed with water (2×200 mL) and the organic phase was concentrated under reduced pressure. The pH of the resulting mixture was adjusted with 1N NaOH to pH 10 and the mixture was then extracted with MTBE. The aqueous phase was cooled to 0° C. to 5° C. and the pH of the aqueous phase was adjusted to pH 3 by adding 1N HCl. The resulting mixture was extracted with DCM and the combined DCM layers were washed with water (1×100 mL), brine (1×100 mL), dried over sodium sulfate and concentrated under vacuum to afford 38 g of the title intermediate (90% purity). MS m/z: [M+H$^+$] calc'd for $C_{18}H_{19}NO_3$ 298.1; found 298.3.

Step B: Preparation of 2-{4-[2-(N-Benzyl-N-methylamino)ethyl]phenyl)ethanol

To a 500-mL three-necked flask, equipped with a magnetic stir bar, nitrogen gas inlet and addition funnel, was added the intermediate from Step A (10 g, 33.6 mmol) and THF (200 mL). The reaction mixture was cooled to 0° C. to 10° C. and lithium aluminum hydride (118 mL, 118 mmol) was added portionwise. The resulting mixture was stirred at ambient temperature for 16 hours and then cooled to 0° C. to 5° C. NaOH (10M) was added slowly, followed by the addition of sodium sulfate. This mixture was stirred for 1 hour and then filtered and concentrated. The pH of the residue was acidified to pH 1 with 1N HCl (100 mL) and the resulting mixture was extracted with EtOAc (3×50 mL). The aqueous phase was cooled to 0° C. to 5° C. and the pH of the aqueous phase was adjusted to pH 14 by the addition of 50% NaOH solution. The resulting mixture was extracted with DCM (3×300 mL) and the combined organic layers were washed with water (100 mL), brine (100 mL), dried over sodium sulfate and concentrated under vacuum to afford 7 g of the title intermediate (7 g, 98.5% purity). MS m/z: [M+H$^+$] calc'd for $C_{18}H_{23}NO$ 270.2; found 270.5.

Step C: Preparation of Toluene-4-sulfonic acid 2-{4-[2-(N-benzyl-N-methylamino)ethyl]phenyl}ethyl ester To a 1-L three-necked flask, equipped with a magnetic stir bar, a nitrogen gas inlet and an addition funnel, was added the intermediate from Step B (22 g, 82 mmol), 1,4-diazabicyclo[2,2,2]octane (13.78 g, 123 mmol) and MTBE (250 mL) and the resulting mixture was cooled to 0° C. to 10° C. A solution of p-toluenesulfonyl chloride (20 g, 94.3 mmol) in MTBE (150 mL) was added slowly and the resulting mixture was stirred at ambient temperature for 5 hours. The mixture was then filtered and concentrated under reduced pressure to provide the title intermediate which was used in the next step without further purification. MS m/z: [M+H$^+$] calc'd for $C_{25}H_{29}NO_3S$ 424.3; found 424.3.

Step D: Preparation of 2-[(S)-1-(2-{4-[2-(N-Benzyl-N-methylamino)ethyl]phenyl}ethyl)pyrrolidin-3-yl]-2,2-diphenylacetamide To a 1-L three-necked flask, equipped with a magnetic stir bar, a nitrogen gas inlet and an addition funnel, was added the intermediate of Step C (40 g, 82 mmol), 2,2-diphenyl-2-(S)-pyrrolidin-3-ylacetamide (23 g, 82 mmol), DIPEA (42.8 mL, 246 mmol) and ACN (400 mL). The resulting mixture was heated at 55° C. for 12 hours and then concentrated under reduced pressure. To the residue was added DCM (1 L) was added and the resulting mixture was washed with water (1×100 mL), 20% ammonium chloride (1×100 mL), brine (1×100 mL), dried over magnesium sulfate and concentrated under vacuum to provide 40 g of crude material which was further purified by silica gel chromatograph and reverse-phase prep-HPLC to afford 10 g of the title intermediate (98.5% purity) as the bis(trifluoroacetate) salt. MS m/z: [M+H$^+$] calc'd for $C_{36}H_{41}N_3O$ 532.3; found 532.3.

Step E: Preparation of 2-((S)-1-{2-[4-(2-Methylaminoethyl)phenyl]ethyl}-pyrrolidin-3-yl)-2,2-diphenylacetamide To a Parr hydrogenation flask was added the intermediate from Step D (6 g, 11.28 mmol), palladium (60 mg, 10 wt. % (dry basis) on activated carbon), isopropanol (60 mL) and water (6 mL). This mixture was degassed with nitrogen and then hydrogen was applied (~50 psi) for 16 hrs. The mixture was filtered and the precipitate washed with isopropanol. The filtrate was condensed and the pH of the resulting mixture was acidified to pH 1 by adding 100 mL of 1N HCl. The resulting mixture was extracted with DCM (3×50 mL) and the aqueous phase was cooled to 0° C. to 5° C. The pH of the aqueous mixture was adjusted to pH 14 by adding 50% NaOH and then the mixture was extracted with DCM (3×200 mL). The combined DCM layers were washed with water (1×100 mL), brine (2×50 mL), dried over sodium sulfate, filtered and concentrated under vacuum to provide 4 g of the title compound (95% purity) as the bis(trifluoroacetate) salt. MS m/z: [M+H$^+$] calc'd for $C_{29}H_{35}N_3O$ 442.3; found 442.5.

Example 3

Synthesis of 2-((S)-1-{2-[3-(2-Methylaminoethyl)phenyl]ethyl}pyrrolidin-3-yl)-2,2-diphenylacetamide

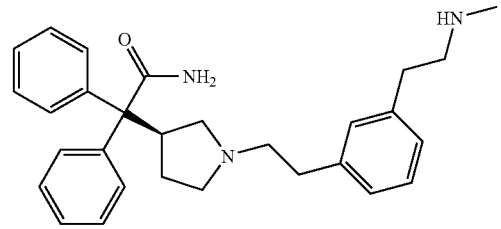

Step A: Preparation of 2-[3-(2-Hydroxyethyl)phenyl]ethanol

To a stirred solution of (3-carboxymethylphenyl)acetic acid (1.0 g, 5.15 mmol) in THF (100 mL) was added slowly borane dimethyl sulfide (2.3 mL, 30.9 mmol). The resulting solution was stirred overnight (~18 hours) and then quenched by slowly adding 1N HCl (100 mL). The mixture was then extracted using EtOAc (3×100 mL) and the combined organic layers were washed with saturated NaCl (100 mL), dried over magnesium sulfate, filtered and concentrated under vacuum to provide 750 mg of the title intermediate (87% yield), which was used without further purification.

Step B: Preparation of 1,3-Bis(2-bromoethyl)benzene

To a flask was added the intermediate from Step A (500 mg, 3.01 mmol) and 48% HBr (5 mL) and the resulting mixture was heated at reflux for 6 hours. The reaction mixture was then cooled to room temperature and diluted with water (100 mL). This mixture was extracted with hexane (1×100 mL) and the organic layer was washed with water (3×100 mL), saturated NaCl (1×100 mL), dried over magnesium sulfate, filtered and concentrated under vacuum to provide 782 mg of the title intermediate (89% yield), which was used without further purification.

Step C: Preparation of 2-((S)-1-{2-[3-(2-Methylaminoethyl)phenyl]ethyl}-pyrrolidin-3-yl)-2,2-diphenylacetamide To a flask was added 2,2-diphenyl-2-(S)-pyrrolidin-3-ylacetamide (42 mg, 0.15 mmol), the intermediate from Step B (44 mg, 0.15 mmol), DMF (1 mL), and potassium carbonate (62 mg, 0.45 mmol) and the resulting mixture was stirred overnight (~18 hours) at room temperature. Methylamine (2.0 M in THF, 375 μL, 0.75 mmol) was then added and stirring was continued at room temperature overnight (18 hours). The reaction mixture was then concentrated under vacuum and to the resulting residue was added 1:1 acetic acid/water (1.0 mL). This mixture was chromatographed using reverse-phase HPLC to obtain 19.8 mg of the title compound (20% yield) as a bis(trifluoroacetate) salt. MS m/z: [M+H$^+$] calc'd for $C_{29}H_{35}N_3O$ 442.3; found 442.6. Retention time=1.90 min (10-70% ACN: $H_2O$, reverse phase HPLC).

Example 4

Synthesis of 2-((S)-1-{3-[5-(3-Methylaminopropyl) thiophen-2-yl]propyl}-pyrrolidin-3-yl)-2,2-diphenylacetamide

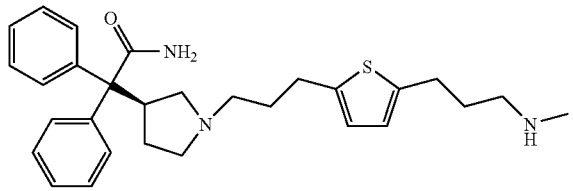

Step A: Preparation of 3-[5-(2-Ethoxycarbonylvinyl) thiophen-2-yl]acrylic Acid Ethyl Ester To a stirred solution of sodium hydride (2.1 g, 53 mmol, 60% in mineral oil) in THF (200 mL) was added slowly triethyl phosphonoacetate (10 mL, 50 mmol). The resulting mixture was stirred until evolution of hydrogen gas ceased (~30 minutes) and then thiophene-2,5-dicarboxaldehyde (3 g, 21 mmol) was added. The resulting mixture was stirred for 1 hour and then the solvent was removed under reduced pressure and DCM (200 mL) was added. The organic layer was washed with water (1×100 mL), 1N HCl (1×100 mL), saturated NaCl (1×100 mL), dried over magnesium sulfate, filtered and the solvent removed under reduced pressure to provide 5.76 g of the title intermediate (98% yield), which was used without further purification.

Step B: Preparation of 3-[5-(2-Ethoxycarbonylethyl)-thiophen-2-yl]propionic Acid Ethyl Ester A stirred solution of the intermediate from Step A (6.0 g, 21 mmol) in MeOH (200 mL) was flushed with nitrogen gas and then palladium (600 mg; 10 wt. % (dry basis) on activated carbon) was added. The reaction flask was placed under vacuum and flushed with hydrogen gas (3 cycles). The reaction mixture was stirred for 1 hour and then flushed with nitrogen gas, filtered and the solvent removed under reduced pressure to afford 6.0 g of the title intermediate (99% yield), which was used without further purification.

Step C: Preparation of 3-[5-(3-Hydroxypropyl)thiophen-2-yl]-propan-1-ol

A stirred solution of DIBAL (88 mL, 88 mmol, 1.0 M in cyclohexane) in THF (300 mL) was cooled to −78° C. and the intermediate from Step B (5.0 g, 17.6 mmol) was added dropwise. After complete addition, the reaction mixture was warmed to ambient temperature over 30 minutes. The reaction was then quenched by slowly adding 1N HCl (200 mL) and then DCM (400 mL) was added. The organic layer was removed and the aqueous layer was washed with DCM (4×100 mL). The combined organic layers were then washed with saturated NaCl (100 mL), dried over magnesium sulfate, filtered and the solvent removed under reduced pressure to provide 3.0 g of the title intermediate (85% yield), which was used without further purification.

Step D: Preparation of 2,5-Bis(3-bromopropyl)thiophene

To a stirred solution of dibromotriphenylphosphorane (10.1 g, 24 mmol) in DCM (150 mL) was added the intermediate from Step C (1.2 g, 6.0 mmol). The reaction was stirred at ambient temperatures overnight (14 hours). The DCM was then removed under reduced pressure and hexane (200 mL) was added to the residue. The heterogeneous mixture was stirred rapidly for 30 minutes and then the hexane was decanted from the insoluble material. The organic layer was then washed with water (2×100 mL), saturated NaCl (1×100 mL), dried over magnesium sulfate, filtered and the solvent removed under reduced pressure to provide 1.5 g of the title intermediate (78% yield), which was used without further purification.

Step E: Preparation of 2-((S)-1-{3-[5-(3-Methylaminopropyl)thiophen-2-yl]propyl}pyrrolidin-3-yl)-2,2-diphenylacetamide To a flask was added 2,2-diphenyl-2-(S)-pyrrolidin-3-ylacetamide (56 mg, 0.2 mmol), the intermediate from Step D (65 mg, 0.2 mmol), DMF (2 mL) and potassium carbonate (83 mg, 0.6 mmol). The resulting mixture was stirred overnight (18 hours) at room temperature. Methylamine (2.0 M in THF, 0.5 mL, 1.0 mmol) was then added and the resulting mixture was stirred at room temperature overnight (18 hours). The reaction mixture was then concentrated under reduced pressure and a 1:1 mixture of acetic acid/water (1.0 mL) was added. This mixture was then chromatographed on reverse-phase HPLC to provide 9.7 mg of the title compound (7% yield) as a bis(trifluoroacetate) salt. MS m/z: [M+H$^+$] calc'd for $C_{29}H_{37}N_3OS$ 476.3; found 476.5. Retention time=2.3 min (10-70 ACN: $H_2O$, reverse phase HPLC).

Example 5

Synthesis of 2-((S)-1-{3-[3-(3-Methylaminopropyl) phenyl]propyl}-pyrrolidin-3-yl)-2,2-diphenylacetamide

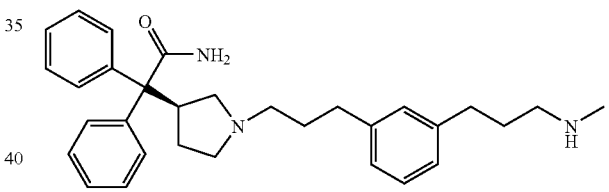

Step A: Preparation of 3-[3-(2-Ethoxycarbonylvinyl)phenyl]-acrylic Acid Ethyl Ester Triethyl phosphonoacetate (17 mL, 85.7 mmol) was slowly added to a stirred solution of sodium hydride (3.7 g, 93.3 mmol, 60% in mineral oil) in THF (200 mL). The resulting mixture was stirred for about 30 minutes until evolution of hydrogen gas ceased. Isophthalaldehyde (5 g, 37.3 mmol) was then added and the reaction mixture was stirred for 4 hours. The reaction mixture was then concentrated under reduced pressure and DCM (200 mL) was added, followed by 1N HCl (100 mL). The organic layer was then removed and washed with water (1×100 mL), saturated NaCl (1×100 mL), dried over magnesium sulfate, filtered and the solvent removed under reduced pressure to provide 9.45 g of the title intermediate (92% yield), which was used without further purification.

Step B: Preparation of 3-[3-(2-Ethoxycarbonylethyl)phenyl]propionic acid Ethyl Ester A stirred solution of the intermediate from Step A (6.5 g, 23.7 mmol) in MeOH (300 mL) was flushed with nitrogen gas and palladium (650 mg; 10 wt. % (dry basis) on activated carbon) was added. The reaction flask was then placed under vacuum and flushed with hydrogen gas (3 cycles). The reaction mixture was stirred overnight (16 hours) and then flushed with nitrogen gas. The mixture was filtered and the solvent removed under reduced pressure to provide 6.2 g of the title intermediate (94% yield), which was used without further purification.

Step C: Preparation of 3-[3-(3-Hydroxypropyl)phenyl]propan-1-ol

A stirred solution of lithium aluminum hydride (1.63 g, 42 mmol) in THF (50 mL) was cooled to 0° C. and the intermediate from Step B (6.0 g, 21 mmol) in THF (50 mL) was added dropwise. After the addition was complete, the reaction mixture was warmed to ambient temperature over 30 minutes. The reaction was quenched by slowly adding 1N HCl (200 mL) and then DCM (400 mL) was added. The organic layer was removed and the aqueous layer was washed with DCM (4×100 mL). The combined organic layers were washed with saturated NaCl (1×100 mL), dried over magnesium sulfate, filtered and the solvent removed under reduced pressure to provide 3.3 g of the title intermediate (81% yield), which was used without further purification.

Step D: Preparation of 1,3-Bis(3-bromopropyl)benzene

To a stirred solution of the intermediate from Step C (2.5 g, 12.8 mmol) was added dibromotriphenylphosphorane (21.7 g, 51.5 mmol) in DCM (200 mL). The resulting mixture was stirred at ambient temperature overnight (24 hours) and then the mixture was concentrated under reduced pressure and hexane (200 mL) was added to the residue. The heterogeneous mixture was stirred rapidly for 30 minutes and then the hexane layer was decanted from the insoluble material. The organic layer was washed with water (2×100 mL), saturated NaCl (1×100 mL), dried over magnesium sulfate, filtered and the solvent removed under reduced pressure to afford 3.14 g of the title intermediate (80% yield), which was used without further purification.

Step E: Preparation of 2-((S)-1-{3-[3-(3-Methylaminopropyl)phenyl]propyl}-pyrrolidin-3-yl)-2,2-diphenylacetamide To a flask was added 2,2-diphenyl-2-(S)-pyrrolidin-3-ylacetamide (880 mg, 1.57 mmol), the intermediate from Step D (1.0 g, 1.57 mmol), ACN (2 mL) and potassium carbonate (1.4 g, 4.7 mmol) and the resulting mixture was stirred overnight (18 hours) at ambient temperature. Methylamine (2.0 M in THF, 7.8 mL, 15.7 mmol) was added and the resulting mixture was stirred at ambient temperature overnight (18 hours). The reaction mixture was concentrated under reduced pressure and a solution of 1:1 acetic acid/water (1.0 mL) was added to the residue. This mixture was chromatographed on reverse phase silica gel (gradient elution, 10-50% ACN/water) to afford 303 mg of the title compound (27% yield) as a bis(trifluoroacetate) salt. MS m/z: [M+H$^+$] calc'd for $C_{31}H_{39}N_3O$ 470.3; found 470.6. Retention time=2.61 min (10-70% ACN: H$_2$O, reverse phase HPLC).

Example 6

Synthesis of 2-((S)-1-{3-[4-(2-Methylaminoethyl)phenyl]propyl}-pyrrolidin-3-yl)-2,2-diphenylacetamide

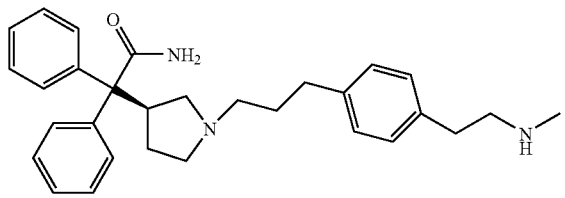

Step A: Preparation of 2-[4-(2-Hydroxyethyl)phenyl]ethan-1-ol

To a stirred solution of (4-carboxymethylphenyl)acetic acid (1.0 g, 5.15 mmol) in THF (100 mL) was slowly added borane dimethyl sulfide (2.3 mL, 30.9 mmol) and the resulting mixture was stirred overnight (~18 hours). The reaction was then quenched by slowly adding 1N HCl (100 mL). The resulting mixture was then extracted with EtOAc (3×100 mL). The combined organic layers were washed with saturated NaCl (1×100 mL), dried over magnesium sulfate, filtered and the solvent removed under reduced pressure to provide 750 mg of the title intermediate (87% yield), which was used without further purification.

Step B: Preparation of Toluene-4-sulfonic Acid 2-[4-(2-Hydroxyethyl-phenyl]ethyl Ester To a stirred solution of the intermediate from Step A in THF (50 mL) was added DABCO (1.51 g, 13.5 mmol) and then p-toluenesulfonyl chloride (50 mL). The resulting mixture was stirred overnight at room temperature and then filtered to remove precipitated hydrochloride salts. The filtrate was concentrated under reduced pressure and DCM (50 mL) was added to the residue. The organic layer was then washed with water (1×100 mL), saturated NaCl (1×100 mL), dried over magnesium sulfate, filtered and the solvent removed under reduced pressure. The resulting material was purified by silica gel chromatography (70% EtOAc/hexane) to afford 1.25 g of the title intermediate (43% yield).

Step C: Preparation of 3-[4-(2-Hydroxyethyl)phenyl]propionitrile

Sodium cyanide (1.8 g, 37 mmol) was added to a stirred solution of the intermediate from Step B (10 g, 31 mmol) in DMSO (100 mL). The mixture was heated to 60° C. overnight (~16 hours) and then the DMSO was removed under reduced pressure. DCM (100 mL) was added to the residue and the resulting mixture was washed with water (1×100 mL), saturated NaCl (1×100 mL), dried over magnesium sulfate, filtered and the solvent removed under reduced pressure to provide 5.4 g of the title intermediate (99% yield), which was used without further purification.

Step D: Preparation of 3-{4-[2-(Benzylmethylamino)ethyl]phenyl}propionitrile

To a stirred solution of the intermediate from Step C (5.4 g, 30.8 mmol) in DCM (250 mL) was added DMSO (7 mL, 123.3 mmol) and DIPEA (16.1 mL, 92.5 mmol). The reaction mixture was then cooled to −15° C. and sulfur trioxide pyridine complex (14.7 g, 92.5 mmol) was added. The resulting mixture was stirred for 2 hours and then the reaction was quenched by adding 1N HCl (250 mL). This mixture was then stirred for 10 minutes and then the organic layer was removed and washed with water (1×250 mL), saturated NaCl (1×250 mL), dried over magnesium sulfate, filtered and the solvent removed under reduced pressure.

The residue was then immediately dissolved in DCM (200 mL) and to this solution was added benzylmethyl amine (6.0 mL, 46.2 mmol) and sodium triacetoxyborohydride (13.6 g, 61.6 mmol). The reaction mixture was stirred overnight (~18 hours) at ambient temperature and then 1N HCl (200 mL) was added. The organic layer was removed and washed with water (1×200 mL), saturated NaCl (1×200 mL), dried over magnesium sulfate, filtered and the solvent removed under reduced pressure. The crude material was purified by silica gel chromatography (5% MeOH/DCM with 0.6% aqueous ammonia) to afford 5.4 g of the title intermediate (52% yield).

Step E: Preparation of 2-[(S)-1-(3-{4-[2-(Benzylmethylamino)-ethyl]phenyl}propyl)pyrrolidin-3-yl]-2,2-diphenylacetamide DIBAL (22 mL, 32 mmol, 25% in toluene) was added to a stirred solution of the intermediate from Step D (4.5 g, 16 mmol) in DCM (200 mL) at −78° C. The reaction was stirred for 3 hours and then MeOH was added until no further hydrogen gas evolution occurred. The mixture was stirred for 10 minutes and then the organic layer was washed with 1N NaOH (1×250 mL), saturated NaCl (1×250 mL), dried over magnesium sulfate, filtered and the solvent removed under reduced pressure.

The residue was immediately dissolved in DCM (450 mL) and to this solution was added 2,2-diphenyl-2-(S)-pyrrolidin-3-ylacetamide (6.0 g, 21.3 mmol) and NaBH(OAc)$_3$ (6.3 g, 28.4 mmol). The resulting mixture was stirred overnight (~21 hours) at ambient temperature and then 1N HCl (200 mL) was added. The organic layer was removed and washed with water (1×200 mL), saturated NaCl (1×200 mL), dried over magnesium sulfate, filtered and the solvent removed under reduced pressure. The crude material was then purified by silica gel chromatography (5% MeOH/DCM with 0.6% aqueous ammonia) to afford 800 mg of the title intermediate (10% yield).

Step F: Preparation of 2-((S)-1-{3-[4-(2-Methylaminoethyl)phenyl]propyl}-pyrrolidin-3-yl)-2,2-diphenylacetamide A stirred solution of the intermediate from Step E (0.8 g, 1.46 mmol) in isopropanol (100 mL) was flushed with nitrogen gas and then palladium (80 mg; 10 wt. % (dry basis) on activated carbon) was added. The reaction flask was then placed under vacuum and then flushed with hydrogen gas (3 cycles). The reaction mixture was then stirred for 2.5 hours and then was flushed with nitrogen gas, filtered and the solvent removed under reduced pressure. To the residue was added a 1:1 mixture of acetic acid/water (1.0 mL) and this mixture was then chromatographed on reverse-phase silica gel (gradient elution, 10-50% ACN/water) to provide 60 mg of the title compound (6% yield) as a bis(trifluoroacetate) salt. MS m/z: [M+H$^+$] calc'd for C$_{30}$H$_{37}$N$_3$O 456.3; found 456.3. Retention time=3.04 min (10-70% ACN: H$_2$O, reverse phase HPLC).

Example 7

Synthesis of 2-[(S)-1-{3-[5-(3-Ethylaminopropyl) thiophen-2-yl]propyl}-pyrrolidin-3-yl]-2,2-diphenylacetamide

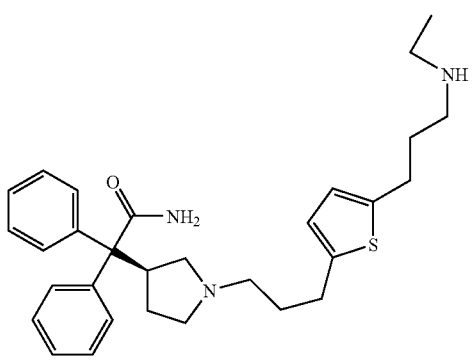

A solution of 2,5-bis(3-bromopropyl)thiophene (32.6 mg, 0.1 mmol), 2,2-diphenyl-2-(S)-pyrrolidin-3-ylacetamide (28.0 mg, 0.1 mmol) and sodium bicarbonate (25.2 mg, 0.3 mmol) in DMF (0.5 mL) was stirred at room temperature for 18 hours. Ethylamine (0.5 mmol) was added and the resulting mixture was stirred at room temperature for about 71 hours. A 1:1 mixture of acetic acid/water (0.8 mL) was then added and this mixture was filtered and purified by HPLC to provide 6.6 mg of the title compound as a bis(trifluoroacetate) salt. MS m/z: [M+H$^+$] calc'd for C$_{30}$H$_{39}$N$_3$OS 490.3; found 490.2.

Example 8

Synthesis of 2-[(S)-1-{3-[5-(3-Isopropylaminopropyl)thiophen-2-yl]propyl}pyrrolidin-3-y]-2,2-diphenylacetamide

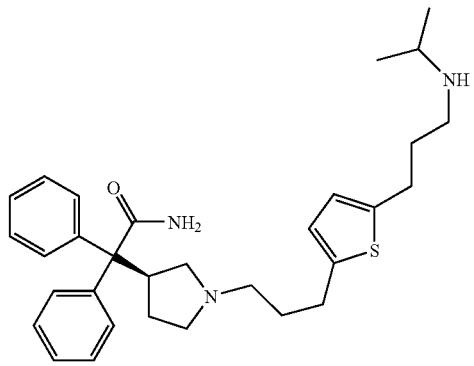

Using the procedure of Example 7 and substituting isopropylamine in place of ethylamine, the title compound was prepared as a bis(trifluoroacetate) salt. MS m/z: [M+H$^+$] calc'd for C$_{31}$H$_{41}$N$_3$OS 504.3; found 504.2.

Example 9

Synthesis of 2-[(S)-1-{3-[5-(3-Dimethylaminopropyl)thiophen-2-yl]-propyl}pyrrolidin-3-yl]-2,2-diphenylacetamide

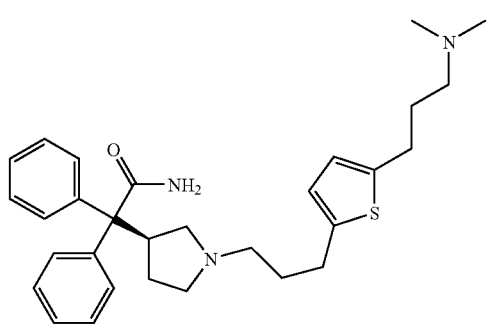

Using the procedure of Example 7 and substituting dimethylamine in place of ethylamine, the title compound was prepared as a bis(trifluoroacetate) salt. MS m/z: [M+H$^+$] calc'd for C$_{30}$H$_{39}$N$_3$OS 490.3; found 490.2.

Example 10

Synthesis of 2-[(S)-1-{2-[4-(2-Ethylaminoethyl) phenyl]ethyl}pyrrolidin-3-yl]-2,2-diphenylacetamide

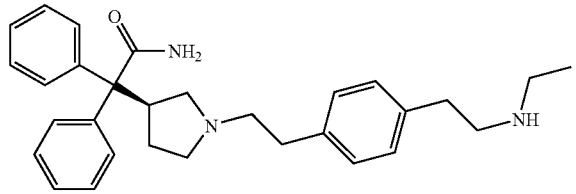

Step A: Preparation of 1,4-Bis(2-bromoethyl)-benzene

Dibromotriphenylphosphorane (5.07 g, 12.0 mmol) was added to a solution of 2-[4-(2-hydroxyethyl)phenyl]ethanol (664.9 mg, 4.0 mmol) in DCM (20 mL, 0.2 M) and the resulting mixture was stirred at room temperature for 18 hours. The reaction mixture was concentrated under reduced pressure and hexane (100 mL) was added to the residue. This mixture was stirred at room temperature for 4 hours and then filtered. The filtrate was concentrated under reduced pressure to provide 1.087 g of the title intermediate as a white solid. The precipitate was washed a second time with hexane (100 mL) and filtered. This filtrate was concentrated under reduced pressure to afford an additional 0.053 g of the title intermediate (combined 97% yield). $^1$H NMR (CDCl$_3$, 300 MHz): δ 7.15-7.16 (br s, 4H), 3.54 (t, J=7.7 Hz, 4H), 3.13 (t, J=7.7 Hz, 4H) ppm.

Step B: Preparation of 2-[(S)-1-{2-[4-(2-ethylaminoethyl) phenyl]ethyl}-pyrrolidin-3-yl]-2,2-diphenylacetamide A solution of 2,2-diphenyl-2-(S)-pyrrolidin-3-ylacetamide (28.0 mg, 0.1 mmol), 1,4-bis(2-bromoethyl)benzene (29.2 mg, 0.1 mmol) and sodium carbonate (41.5 mg, 0.3 mmol) in DMF (0.5 mL) was stirred at room temperature for 18 hours. Ethylamine (0.5 mmol) was added and the resulting mixture was stirred at room temperature for about 71 hours. A 1:1 mixture of acetic acid/water (0.8 mL) was then added and this mixture was filtered and purified by RP-HPLC to provide 25.1 mg of the title compound as a bis(trifluoroacetate) salt. MS m/z: [M+H$^+$] calc'd for C$_{30}$H$_{37}$N$_3$O 456.3; found 456.2.

Using the procedures above and substituting the appropriate starting materials, the following compounds were prepared:

| Ex. | Compound | MS[1] |
|---|---|---|
| 11 | 2-[(S)-1-{2-[4-(2-isopropylaminoethyl)phenyl]ethyl} pyrrolidin-3-yl]-2,2-diphenylacetamide | 470.2 |
| 12 | 2-[(S)-1-{2-[4-(2-dimethylaminoethyl)phenyl]ethyl} pyrrolidin-3-yl]-2,2-diphenylacetamide | 456.2 |
| 13 | 2,2-diphenyl-2-[(S)-1-{2-[4-(2-pyrrolidin-1-ylethyl)phenyl]ethyl}pyrrolidin-3-yl]acetamide | 482.2 |
| 14 | 2-[(S)-1-(2-{4-[2-(benzylmethylamino)ethyl]phenyl} ethyl)pyrrolidin-3-yl]-2,2-diphenylacetamide | — |
| 15 | 2-[(S)-1-(2-{4-[2-(2-acetylaminoethylamino)ethyl] phenyl}ethyl)pyrrolidin-3-yl]-2,2-diphenylacetamide | 513.2 |
| 16 | 2-{(S)-1-[2-(4-{2-[(5-methylpyrazin-2-ylmethyl)amino] ethyl}phenyl)ethyl]pyrrolidin-3-yl}-2,2-diphenylacetamide | 534.2 |
| 17 | 2-{(S)-1-[2-(4-{2-[(furan-2-ylmethyl)amino]ethyl} phenyl)ethyl]-pyrrolidin-3-yl}-2,2-diphenylacetamide | 508.2 |
| 18 | 2-{(S)-1-[2-(4-{2-[(benzo[1,3]dioxol-5-ylmethyl)amino] ethyl}phenyl)ethyl]pyrrolidin-3-yl}-2,2-diphenylacetamide | 562.2 |
| 19 | 2-((S)-1-{2-[4-(2-azetidin-1-ylethyl)phenyl]ethyl}pyrrolidin-3-yl)-2,2-diphenylacetamide | 468.2 |
| 20 | 2-[(S)-1-(3-{5-[3-(2-acetylaminoethylamino)propyl]thiophen-2-yl}propyl)pyrrolidin-3-yl]-2,2-diphenylacetamide | 547.2 |
| 21 | 2-{(S)-1-[3-(5-{3-[(5-methylpyrazin-2-ylmethyl)amino] propyl}thiophen-2-yl)propyl]pyrrolidin-3-yl}-2,2-diphenylacetamide | 568.2 |
| 22 | 2-{(S)-1-[3-(5-{3-[(furan-2-ylmethyl)amino]propyl}thiophen-2-yl)-propyl]pyrrolidin-3-yl}-2,2-diphenylacetamide | 542.2 |
| 23 | 2-{(S)-1-[3-(5-{3-[(benzo[1,3]dioxol-5-ylmethyl)amino] propyl}thiophen-2-yl)propyl]pyrrolidin-3-yl}-2,2-diphenylacetamide | 596.2 |
| 24 | 2-[(S)-1-(3-{5-[3-(4-methylpiperazin-1-yl)propyl] thiophen-2-yl}propyl)pyrrolidin-3-yl]-2,2-diphenylacetamide | 545.2 |
| 25 | 2-((S)-1-{3-[5-(3-morpholin-4-yl-propyl)thiophen-2-yl]propyl}-pyrrolidin-3-yl)-2,2-diphenylacetamide | 532.2 |
| 26 | 2-((S)-1-{3-[5-(3-azetidin-1-ylpropyl)thiophen-2-yl]propyl}pyrrolidin-3-yl)-2,2-diphenylacetamide | 502.2 |

[1]Observed m/z [M + H$^+$], unless otherwise indicated.

Assay 1

Radioligand Binding Assay

A. Membrane Preparation from Cells Expressing hM$_1$, hM$_2$, hM$_3$ and hM$_4$ Muscarinic Receptor Subtypes CHO cell lines stably expressing cloned human hM$_1$, hM$_2$, hM$_3$ and hM$_4$ muscarinic receptor subtypes, respectively, were grown to near confluency in medium consisting of HAM's F-12 supplemented with 10% FBS and 250 µg/mL Geneticin. The cells were grown in a 5% CO$_2$, 37° C. incubator and lifted with 2 mM EDTA in dPBS. Cells were collected by 5 minute centrifugation at 650×g, and cell pellets were either stored frozen at −80° C. or membranes were prepared immediately. For membrane preparation, cell pellets were suspended in lysis buffer and homogenized with a Polytron PT-2100 tissue disrupter (Kinematica AG; 20 seconds×2 bursts). Crude membranes were centrifuged at 40,000×g for 15 minutes at 4° C. The membrane pellet was then resuspended with resuspension buffer and homogenized again with the Polytron tissue disrupter. The protein concentration of the membrane suspension was determined by the method described in Lowry, O. et al., *Journal of Biochemistry* 193:265 (1951). All membranes were stored frozen in aliquots at −80° C. or used immediately. Aliquots of prepared hM$_5$ receptor membranes were purchased directly from Perkin Elmer and stored at −80° C. until use.

B. Radioligand Binding Assay on Muscarinic Receptor Subtypes hM$_1$, hM$_2$, hM$_3$, hM$_4$ and hM$_5$ Radioligand binding assays were performed in 96-well microtiter plates in a total assay volume of 100 µL. CHO cell membranes stably expressing either the hM$_1$, hM$_2$, hM$_3$, hM$_4$ or hM$_5$ muscarinic subtype were diluted in assay buffer to the following specific target protein concentrations (µg/ well): 10 µg for hM$_1$, 10-15 µg for hM$_2$, 10-20 µg for hM$_3$, 10-20 µg for hM$_4$, and 10-12 µg for hM$_5$. The membranes were briefly homogenized using a Polytron tissue disruptor (10 seconds) prior to assay plate addition. Saturation binding studies for determining K$_D$ values of the radioligand were performed using L-[N-methyl-$^3$H]scopolamine methyl chloride ([$^3$H]-NMS) (TRK666, 84.0 Ci/mmol, Amersham Pharmacia Biotech, Buckinghamshire, England) at concentrations ranging from 0.001 nM to 20 nM. Displacement assays for determination of $K_i$ values of test compounds were performed with [$^3$H]-NMS at 1 nM and eleven different test compound concentrations. The test compounds were initially dissolved to a concentration of 400 μM in dilution buffer and then serially diluted 5× with dilution buffer to final concentrations ranging from 10 pM to 100 μM. The addition order and volumes to the assay plates were as follows: 25 μL radioligand, 25 μL diluted test compound, and 50 μL membranes. Assay plates were incubated for 60 minutes at 37° C. Binding reactions were terminated by rapid filtration over GF/B glass fiber filter plates (Perkin Elmer Inc., Wellesley, Mass.) pre-treated in 1% BSA. Filter plates were rinsed three times with wash buffer (10 mM HEPES) to remove unbound radioactivity. Plates were then air dried, and 50 μL Microscint-20 liquid scintillation fluid (PerkinElmer Inc., Wellesley, Mass.) was added to each well. The plates were then counted in a PerkinElmer Topcount liquid scintillation counter (PerkinElmer Inc., Wellesley, Mass.). Binding data were analyzed by nonlinear regression analysis with the GraphPad Prism Software package (GraphPad Software, Inc., San Diego, Calif.) using the one-site competition model. $K_i$ values for test compounds were calculated from observed $IC_{50}$ values and the $K_D$ value of the radioligand using the Cheng-Prusoff equation (Cheng Y; Prusoff W. H. *Biochemical Pharmacology* 22(23):3099-108 (1973)). $K_i$ values were converted to $pK_i$ values to determine the geometric mean and 95% confidence intervals. These summary statistics were then converted back to $K_i$ values for data reporting.

In this assay, a lower $K_i$ value indicates that the test compound has a higher binding affinity for the receptor tested. Exemplary compounds of the invention that were tested in this assay, were found to have a $K_i$ value of less than about 100 nM for the $M_3$ muscarinic receptor subtype in this assay (except the compound of Example 16 which had a $K_i$ of 110 nM for the $M_3$ muscarinic receptor). In particular, the compounds of Examples 1 to 12 were found to have $K_i$ values of less than 10 nM for the $M_3$ muscarinic receptor.

Assay 2

Muscarinic Receptor Functional Potency Assays

A. Blockade of Agonist-Mediated Inhibition of cAMP Accumulation

In this assay, the functional potency of a test compound is determined by measuring the ability of the test compound to block oxotremorine-inhibition of forskolin-mediated cAMP accumulation in CHO-K1 cells expressing the $hM_2$ receptor.

cAMP assays are performed in a radioimmunoassay format using the Flashplate Adenylyl Cyclase Activation Assay System with $^{125}$I-cAMP (NEN SMP004B, PerkinElmer Life Sciences Inc., Boston, Mass.), according to the manufacturer's instructions.

Cells are rinsed once with dPBS and lifted with Trypsin-EDTA solution (0.05% trypsin/0.53 mM EDTA) as described in the Cell Culture and Membrane Preparation section above. The detached cells are washed twice by centrifugation at 650×g for five minutes in 50 mLs dPBS. The cell pellet is then re-suspended in 10 mL dPBS, and the cells are counted with a Coulter Z1 Dual Particle Counter (Beckman Coulter, Fullerton, Calif.). The cells are centrifuged again at 650×g for five minutes and re-suspended in stimulation buffer to an assay concentration of $1.6 \times 10^6$-$2.8 \times 10^6$ cells/mL.

The test compound is initially dissolved to a concentration of 400 μM in dilution buffer (dPBS supplemented with 1 mg/mL BSA (0.1%)), and then serially diluted with dilution buffer to final molar concentrations ranging from 100 μM to 0.1 nM. Oxotremorine is diluted in a similar manner.

To measure oxotremorine inhibition of AC activity, 25 μL forskolin (25 μM final concentration diluted in dPBS), 25 μL diluted oxotremorine, and 50 μL cells are added to agonist assay wells. To measure the ability of a test compound to block oxotremorine-inhibited AC activity, 25 μL forskolin and oxotremorine (25 μM and 5 μM final concentrations, respectively, diluted in dPBS) 25 μL diluted test compound, and 50 μL cells are added to remaining assay wells.

Reactions are incubated for 10 minutes at 37° C. and stopped by addition of 100 μL ice-cold detection buffer. Plates are sealed, incubated overnight at room temperature and counted the next morning on a PerkinElmer TopCount liquid scintillation counter (PerkinElmer Inc., Wellesley, Mass.). The amount of cAMP produced (pmol/well) is calculated based on the counts observed for the samples and cAMP standards, as described in the manufacturer's user manual. Data are analyzed by nonlinear regression analysis with the GraphPad Prism Software package (GraphPad Software, Inc., San Diego, Calif.) using the non-linear regression, one-site competition equation. The Cheng-Prusoff equation is used to calculate the $K_i$, using the $EC_{50}$ of the oxotremorine concentration-response curve and the oxotremorine assay concentration as the $K_D$ and [L], respectively. The $K_i$ values are converted to $pK_i$ values to determine the geometric mean and 95% confidence intervals. These summary statistics are then converted back to $K_i$ values for data reporting.

In this assay, a lower $K_i$ value indicates that the test compound has a higher functional activity at the receptor tested. The exemplified compounds of this invention are expected to have a $K_i$ value of less than about 100 nM for blockade of oxotremorine-inhibition of forskolin-mediated cAMP accumulation in CHO-K1 cells expressing the $hM_2$ receptor.

B. Blockade of Agonist-Mediated [$^{35}$S]GTPγS Binding

In a second functional assay, the functional potency of test compounds can be determined by measuring the ability of the compounds to block oxotremorine-stimulated [$^{35}$S] GTPγS binding in CHO-K1 cells expressing the $hM_2$ receptor.

At the time of use, frozen membranes are thawed and then diluted in assay buffer with a final target tissue concentration of 5-10 μg protein per well. The membranes are briefly homogenized using a Polytron PT-2100 tissue disrupter and then added to the assay plates.

The $EC_{90}$ value (effective concentration for 90% maximal response) for stimulation of [$^{35}$S]GTPγS binding by the agonist oxotremorine is determined in each experiment.

To determine the ability of a test compound to inhibit oxotremorine-stimulated [$^{35}$S]GTPγS binding, the following is added to each well of 96 well plates: 25 μL of assay buffer with [$^{35}$S]GTPγS (0.4 nM), 25 μL of oxotremorine($EC_{90}$) and GDP (3 μM), 25 μL of diluted test compound and 25 μL CHO cell membranes expressing the $hM_2$ receptor. The assay plates are then incubated at 37° C. for 60 minutes. The assay plates are filtered over 1% BSA-pretreated GF/B filters using a PerkinElmer 96-well harvester. The plates are rinsed with ice-cold wash buffer for 3×3 seconds and then air or vacuum dried. Microscint-20 scintillation liquid (50 μL) is added to each well, and each plate is sealed and radioactivity counted on a topcounter (PerkinElmer). Data are analyzed by nonlinear regression analysis with the GraphPad Prism Software package (GraphPad Software, Inc., San Diego, Calif.) using the non-linear regression, one-site competition equation. The Cheng-Prusoff equation is used to calculate the $K_i$, using the $IC_{50}$ values of the concentration-response curve for the test compound and the oxotremorine concentration in the assay as the $K_D$ and [L], ligand concentration, respectively.

In this assay, a lower $K_i$ value indicates that the test compound has a higher functional activity at the receptor tested. The exemplified compounds of this invention are expected to have a $K_i$ value of less than about 100 nM for blockade of oxotremorine-stimulated [$^{35}$S]GTPγS binding in CHO-K1 cells expressing the $hM_2$ receptor.

C. Blockade of Agonist-Mediated Calcium Release via FLIPR Assays

Muscarinic receptor subtypes ($M_1$, $M_3$ and $M_5$ receptors), which couple to $G_q$ proteins, activate the phospholipase C (PLC) pathway upon agonist binding to the receptor. As a result, activated PLC hydrolyzes phosphatyl inositol diphosphate ($PIP_2$) to diacylglycerol (DAG) and phosphatidyl-1,4,5-triphosphate ($IP_3$), which in turn generates calcium release from intracellular stores, i.e., endoplasmic and sarcoplasmic reticulum. The FLIPR (Molecular Devices, Sunnyvale, Calif.) assay capitalizes on this increase in intracellular calcium by using a calcium sensitive dye (Fluo-4AM, Molecular Probes, Eugene, Oreg.) that fluoresces when free calcium binds. This fluorescence event is measured in real time by the FLIPR, which detects the change in fluorescence from a monolayer of cells cloned with human $M_1$ and $M_3$, and chimpanzee $M_5$ receptors. Antagonist potency can be determined by the ability of antagonists to inhibit agonist-mediated increases in intracellular calcium.

For FLIPR calcium stimulation assays, CHO cells stably expressing the $hM_1$, $hM_3$ and $cM_5$ receptors are seeded into 96-well FLIPR plates the night before the assay is done. Seeded cells are washed twice by Cellwash (MTX Labsystems, Inc.) with FLIPR buffer (10 mM HEPES, pH 7.4, 2 mM calcium chloride, 2.5 mM probenecid in Hank's Buffered Salt Solution (HBSS) without calcium and magnesium) to remove growth media and leaving 50 µL/well of FLIPR buffer. The cells are then incubated with 50 µL/well of 4 µM FLUO-4AM (a 2× solution was made) for 40 minutes at 37° C., 5% carbon dioxide. Following the dye incubation period, cells are washed two times with FLIPR buffer, leaving a final volume of 50 µL/well.

To determine antagonist potency, the dose-dependent stimulation of intracellular $Ca^{2+}$ release for oxotremorine is first determined so that antagonist potency can later be measured against oxotremorine stimulation at an $EC_{90}$ concentration. Cells are first incubated with compound dilution buffer for 20 minutes, followed by agonist addition, which is performed by the FLIPR. An $EC_{90}$ value for oxotremorine is generated according to the method detailed in the FLIPR measurement and data reduction section below, in conjunction with the formula $EC_F=((F/100-F)^{\wedge}1/H)*EC_{50}$. An oxotremorine concentration of $3 \times EC_F$ is prepared in stimulation plates such that an $EC_{90}$ concentration of oxotremorine is added to each well in the antagonist inhibition assay plates.

The parameters used for the FLIPR are: exposure length of 0.4 seconds, laser strength of 0.5 watts, excitation wavelength of 488 nm, and emission wavelength of 550 nm. Baseline is determined by measuring the change in fluorescence for 10 seconds prior to addition of agonist. Following agonist stimulation, the FLIPR continuously measured the change of fluorescence every 0.5 to 1 second for 1.5 minutes to capture the maximum fluorescence change.

The change of fluorescence is expressed as maximum fluorescence minus baseline fluorescence for each well. The raw data is analyzed against the logarithm of drug concentration by nonlinear regression with GraphPad Prism (GraphPad Software, Inc., San Diego, Calif.) using the built-in model for sigmoidal dose-response. Antagonist $K_i$ values are determined by Prism using the oxotremorine $EC_{50}$ value as the $K_D$ and the oxotremorine $EC_{90}$ for the ligand concentration according to the Cheng-Prusoff equation (Cheng & Prusoff, 1973).

In this assay, a lower $K_i$ value indicates that the test compound has a higher functional activity at the receptor tested. The exemplified compounds of this invention are expected to have a $K_i$ value of less than about 100 nM for blockade of agonist-mediated calcium release in CHO cells stably expressing the $hM_3$ receptor.

Assay 3

Determination of Duration of Bronchoprotection in Guinea Pig Model of Acetylcholine-Induced Bronchoconstriction This in vivo assay was used to assess the bronchoprotective effects of test compounds exhibiting muscarinic receptor antagonist activity.

Groups of six male guinea pigs (Duncan-Hartley (Hsd-Poc:DH) Harlan, Madison, Wis.) weighing between 250 and 350 g were individually identified by cage cards. Throughout the study animals were allowed access to food and water ad libitum.

Test compounds were administered via inhalation over 10 minutes in a whole-body exposure dosing chamber (R&S Molds, San Carlos, Calif.). The dosing chambers were arranged so that an aerosol was simultaneously delivered to 6 individual chambers from a central manifold. Guinea pigs were exposed to an aerosol of a test compound or vehicle (WFI). These aerosols were generated from aqueous solutions using an LC Star Nebulizer Set (Model 22F51, PARI Respiratory Equipment, Inc. Midlothian, Va.) driven by a mixture of gases ($CO_2$=5%, $O_2$=21% and $N_2$=74%) at a pressure of 22 psi. The gas flow through the nebulizer at this operating pressure was approximately 3 L/minute. The generated aerosols were driven into the chambers by positive pressure. No dilution air was used during the delivery of aerosolized solutions. During the 10 minute nebulization, approximately 1.8 mL of solution was nebulized. This was measured gravimetrically by comparing pre-and post-nebulization weights of the filled nebulizer.

The bronchoprotective effects of test compounds administered via inhalation were evaluated using whole body plethysmography at 1.5, 24, 48 and 72 hours post-dose.

Forty-five minutes prior to the start of the pulmonary evaluation, each guinea pig was anesthetized with an intramuscular injection of ketamine (43.75 mg/kg), xylazine (3.50 mg/kg) and acepromazine (1.05 mg/kg). After the surgical site was shaved and cleaned with 70% alcohol, a 2-3 cm midline incision of the ventral aspect of the neck was made. Then, the jugular vein was isolated and cannulated with a saline-filled polyethylene catheter (PE-50, Becton Dickinson, Sparks, Md.) to allow for intravenous infusions of ACh (Sigma-Aldrich, St. Louis, Mo.) in saline. The trachea was then dissected free and cannulated with a 14 G teflon tube (#NE-014, Small Parts, Miami Lakes, Fla.). If required, anesthesia was maintained by additional intramuscular injections of the aforementioned anesthetic mixture. The depth of anesthesia was monitored and adjusted if the animal responded to pinching of its paw or if the respiration rate was greater than 100 breaths/minute.

Once the cannulations were complete, the animal was placed into a plethysmograph (#PLY3114, Buxco Electronics, Inc., Sharon, Conn.) and an esophageal pressure cannula (PE-160, Becton Dickinson, Sparks, Md.) was inserted to measure pulmonary driving pressure (pressure). The teflon tracheal tube was attached to the opening of the plethysmograph to allow the guinea pig to breathe room air from outside the chamber. The chamber was then sealed. A heating lamp was used to maintain body temperature and the guinea pig's lungs were inflated 3 times with 4 mL of air using a 10 mL calibration syringe (#5520 Series, Hans Rudolph, Kansas City, Mo.) to ensure that the lower airways did not collapse and that the animal did not suffer from hyperventilation.

Once it was determined that baseline values were within the range 0.3-0.9 mL/cm $H_2O$ for compliance and within the range 0.1-0.199 cm $H_2O$/mL per second for resistance, the pulmonary evaluation was initiated. A Buxco pulmonary measurement computer progam enabled the collection and derivation of pulmonary values.

Starting this program initiated the experimental protocol and data collection. The changes in volume over time that occur within the plethysmograph with each breath were measured via a Buxco pressure transducer. By integrating this signal over time, a measurement off low was calculated for each breath. This signal, together with the pulmonary driving pressure changes, which were collected using a Sensym pressure transducer (#TRD4100), was connected via a Buxco (MAX 2270) preamplifier to a data collection interface (#'s SFT3400 and SFT3813). All other pulmonary parameters were derived from these two inputs.

Baseline values were collected for 5 minutes, after which time the guinea pigs were challenged with ACh. ACh (0.1 mg/mL) was infused intravenously for 1 minute from a syringe pump (sp210iw, World Precision Instruments, Inc., Sarasota, Fla.) at the following doses and prescribed times from the start of the experiment: 1.9 μg/minute at 5 minutes, 3.8 μg/minute at 10 minutes, 7.5 μg/minute at 15 minutes, 15.0 μg/minute at 20 minutes, 30 μg/minute at 25 minutes and 60 μg/minute at 30 minutes. If resistance or compliance had not returned to baseline values at 3 minutes following each ACh dose, the guinea pig's lungs were inflated 3 times with 4 mL of air from a 10 mL calibration syringe. Recorded pulmonary parameters included respiration frequency (breaths/minute), compliance (mL/cm $H_2O$) and pulmonary resistance (cm $H_2O$/mL per second). Once the pulmonary function measurements were completed at minute 35 of this protocol, the guinea pig was removed from the plethysmograph and euthanized by carbon dioxide asphyxiation.

The data were evaluated in one or both of the following ways:

(a) Pulmonary resistance ($R_L$, cm $H_2O$/mL per second) was calculated from the ratio of "change in pressure" to "the change in flow." The $R_L$ response to ACh (60 μg/min, IH) was computed for the vehicle and the test compound groups. The mean ACh response in vehicle-treated animals, at each pre-treatment time, was calculated and used to compute % inhibition of ACh response, at the corresponding pre-treatment time, at each test compound dose. Inhibition dose-response curves for '$R_L$' were fitted with a four parameter logistic equation using GraphPad Prism, version 3.00 for Windows (GraphPad Software, San Diego, Calif.) to estimate bronchoprotective $ID_{50}$ (dose required to inhibit the ACh (60 μg/min) bronchoconstrictor response by 50%). The equation used was as follows:

$$Y = Min + (Max - Min)/(1 + 10^{((\log ID50 - X)*Hillslope)})$$

where X is the logarithm of dose, Y is the response (% Inhibition of ACh induced increase in $R_L$). Y starts at Min and approaches asymptotically to Max with a sigmoidal shape.

(b) The quantity $PD_2$, which is defined as the amount of ACh or histamine needed to cause a doubling of the baseline pulmonary resistance, was calculated using the pulmonary resistance values derived from the flow and the pressure over a range of ACh or histamine challenges using the following equation (which is derived from a equation used to calculate $PC_{20}$ values described in American Thoracic Society. Guidelines for methacholine and exercise challenge testing—1999. *Am J Respir Crit Care Med*. 161: 309-329 (2000)):

$$PD_2 = \text{antilog}\left[\log C_1 + \frac{(\log C_2 - \log C_1)(2R_0 - R_1)}{R_2 - R_1}\right]$$

where:

$C_1$=concentration of ACh or histamine preceding $C_2$ $C_2$=concentration of ACh or histamine resulting in at least a 2-fold increase in pulmonary resistance ($R_L$)

$R_0$=Baseline $R_L$ value $R_1$=$R_L$ value after $C_1$ $R_2$=$R_L$ value after $C_2$ An efficacious dose was defined as a dose that limited the bronchrestriction response to a 50 μg/mL dose of ACh to a doubling of the baseline pulmonary resistance ($PD_{2(50)}$). Statistical analysis of the data was performed using a two-tailed Students t-test. A P-value<0.05 was considered significant.

Generally, test compounds having a $PD_{2(50)}$ less than about 300 μg/mL for ACh-induced bronchoconstriction at 1.5 hours post-dose in this assay are preferred. For example, the compounds of Examples 2 and 3 were found to have a $PD_{2(50)}$ less than about 300 μg/mL for ACh-induced bronchoconstriction at 1.5 hours post-dose.

Assay 4

Inhalation Guinea Pig Salivation Assay

Guinea pigs (Charles River, Wilmington, Mass.) weighing 200-350 g were acclimated to the in-house guinea pig colony for at least 3 days following arrival. Test compound or vehicle were dosed via inhalation (IH) over a 10 minute time period in a pie shaped dosing chamber (R&S Molds, San Carlos, Calif.). Test solutions were dissolved in sterile water and delivered using a nebulizer filled with 5.0 mL of dosing solution. Guinea pigs were restrained in the inhalation chamber for 30 minutes. During this time, guinea pigs were restricted to an area of approximately 110 sq. cm. This space was adequate for the animals to turn freely, reposition themselves, and allow for grooming. Following 20 minutes of acclimation, guinea pigs were exposed to an aerosol generated from a LS Star Nebulizer Set (Model 22F51, PARI Respiratory Equipment, Inc. Midlothian, Va.) driven by house air at a pressure of 22 psi. Upon completion of nebulization, guinea pigs were evaluated at 1.5, 6, 12, 24, 48, or 72 hrs after treatment.

Guinea pigs were anesthetized one hour before testing with an intramuscular (IM) injection of a mixture of ketamine 43.75 mg/kg, xylazine 3.5 mg/kg, and acepromazine 1.05 mg/kg at an 0.88 mL/kg volume. Animals were placed ventral side up on a heated (37° C.) blanket at a 20 degree incline with their head in a downward slope. A 4-ply 2×2 inch gauze pad (Nu-Gauze General-use sponges, Johnson and Johnson, Arlington, Tex.) was inserted in the guinea pig's mouth. Five minutes later, the muscarinic agonist pilocarpine (3.0 mg/kg, SC) was administered and the gauze pad was immediately discarded and replaced by a new pre-weighed gauze pad. Saliva was collected for 10 minutes, at which point the gauze pad was weighed and the difference in weight recorded to determine the amount of accumulated saliva (in mg). The mean amount of saliva collected for animals receiving the vehicle and each dose of test compound was calculated. The vehicle group mean was considered to be 100% salivation. Results were calculated using result means (n=3 or greater). Confidence intervals (95%) were calculated for each dose at each time point using two-way ANOVA. This model is a modified version of the procedure described in Rechter, "Estimation of anticholinergic drug effects in mice by antagonism against pilocarpine-induced salivation" *Ata Pharmacol Toxicol* 24:243-254 (1996)

The mean weight of saliva in vehicle-treated animals, at each pre-treatment time, was calculated and used to compute % inhibition of salivation, at the corresponding pre-treatment time, at each dose. The inhibition dose-response data were fitted to a four parameter logistic equation using GraphPad Prism, version 3.00 for Windows (GraphPad Software, San Diego, Calif.) to estimate anti-sialagogue $ID_{50}$ (dose required to inhibit 50% of pilocarpine-evoked salivation). The equation used was as follows:

$$Y = Min + (Max - Min)/(1 + 10^{((\log ID50 - X) * Hillslope)})$$

where X is the logarithm of dose, Y is the response (% inhibition of salivation). Y starts at Min and approaches asymptotically to Max with a sigmoidal shape.

The ratio of the anti-sialagogue $ID_{50}$ to bronchoprotective $ID_{50}$ was used to compute the apparent lung selectivity index of the test compound. Generally, compounds having an apparent lung selectivity index greater than about 5 are preferred. In this assay, the compound of Example 2 had an apparent lung-selectivity index greater than about 15.

Assay 5

Methacholine-Induced Depressor Responses in Conscious Guinea Pigs

Healthy, adult, male Sprague-Dawley guinea pigs (Harlan, Indianapolis, Ind.), weighing between 200 and 300 g are used in these studies. Under isoflurane anesthesia (to effect), animals are instrumented with common carotid artery and jugular vein catheters (PE-50 tubing). The catheters are exteriorized utilizing a subcutaneous funnel to the subscapular area. All surgical incisions are sutured with 4-0 Ethicon Silk and the catheters locked with heparin (1000 units/mL). Each animal is administered saline (3 mL, SC) at the end of surgery as well as buprenorphine (0.05 mg/kg, IM). Animals are allowed to recover on a heating pad before being returned to their holding rooms.

Approximately 18 to 20 hours following surgery, the animals are weighed and the carotid artery catheter on each animal is connected to a transducer for recording arterial pressure. Arterial pressure and heart rate is recorded using a Biopac MP-100 Acquisition System. Animals are allowed to acclimate and stabilize for a period of 20 minutes.

Each animal is challenged with MCh (0.3 mg/kg, IV) administered through the jugular venous line and the cardiovascular response is monitored for 10 minutes. The animals are then placed into the whole body dosing chamber, which is connected to a nebulizer containing the test compound or vehicle solution. The solution is nebulized for 10 minutes using a gas mixture of breathable air and 5% carbon dioxide with a flow rate of 3 liters/minute. The animals are then removed from the whole body chamber and returned to their respective cages. At 1.5 and 24 h post-dosing, the animals are re-challenged with MCh (0.3 mg/kg, IV) and the hemodynamic response is determined. Thereafter, the animals are euthanized with sodium pentobarbital (150 mg/kg, IV).

MCh produces a decrease in mean arterial pressure (MAP) and decrease in heart rate (bradycardia). The peak decrease, from baseline, in MAP (depressor responses) was measured for each MCh challenge (before and after IH dosing). The bradycardic effects are not used for analysis since these responses are not robust and reproducible. The effects of treatment on the MCh responses are expressed as % inhibition (mean+/–SEM) of the control depressor responses. Two-way ANOVA with the appropriate post-hoc test was used to test the effects of treatment and pre-treatment time. The depressor responses to MCh were relatively unchanged at 1.5 and 24 h after inhalation dosing with vehicle.

The ratio of the anti-depressor $ID_{50}$ to bronchoprotective $ID_{50}$ was used to compute apparent lung-selectivity of the test compound. Generally, compounds having an apparent lung-selectivity index greater than 5 are preferred. In this assay, compounds of the invention are expected to have an apparent lung-selectivity index greater than 5.

While the present invention has been described with reference to specific aspects or embodiments thereof, it will be understood by those of ordinary skilled in the art that various changes can be made or equivalents can be substituted without departing from the true spirit and scope of the invention. Additionally, to the extent permitted by applicable patent statues and regulations, all publications, patents and patent applications cited herein are hereby incorporated by reference in their entirety to the same extent as if each document had been individually incorporated by reference herein.

What is claimed is:

1. A compound of formula I:

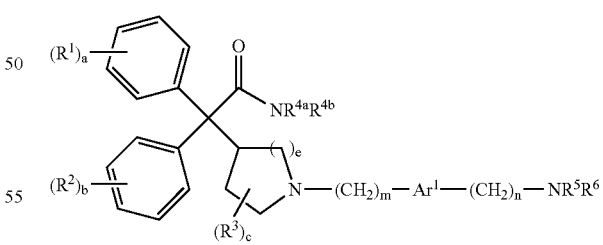

wherein:
each $R^1$ and $R^2$ are independently selected from (1-4C)alkyl, (2-4C)alkenyl, (2-4C)alkynyl, (3-6C)cycloalkyl, cyano, halo, —$OR^a$, —$SR^a$, —$NR^aR^b$, —$S(O)R^c$ and —$S(O)_2R^c$; where each $R^a$ and $R^b$ independently represents hydrogen, (1-4C)alkyl, (2-4C)alkenyl, (2-4C)alkynyl or (3-6C)cycloalkyl; each $R^c$ independently represents (1-4C)alkyl, (2-4C)alkenyl, (2-4C)alkynyl or (3-6C)cycloalkyl; or two adjacent $R^1$ groups or two adjacent $R^2$ groups are joined together to form (3-6C) alkylene, (2-4C)alkylene-O— or —O—(2-4C)alkylene-O—;

a and b each independently are 0 or an integer of from 1 to 5;

each $R^3$ independently is fluoro or (1-4C)alkyl;

c is 0 or an integer of from 1 to 3;

$R^{4a}$ and $R^{4b}$ are independently selected from hydrogen, (1-4C)alkyl and phenyl-(1-4C)alkyl; or $R^{4a}$ and $R^{4b}$ together with the carbon atom to which they are attached form a (3-6C)heterocyclic ring optionally containing one additional heteroatom selected from nitrogen, oxygen or sulfur and wherein the heterocyclic ring is unsubstituted or substituted with 1 or 2 substituents selected independently from (1-4C)alkyl and fluoro;

e is 1;

m is 1, 2, 3 or 4;

$Ar^1$ represents a phenylene group or a (3-5C)heteroarylene group containing 1 or 2 heteroatoms selected independently from oxygen, nitrogen or sulfur; wherein the phenylene and heteroarylene groups are unsubstituted or substituted with 1 to 4 substituents selected independently from halo, (1-4C)alkyl or (1-4C)alkoxy; wherein each alkyl and alkoxy group is optionally substituted with from 1 to 3 fluoro substituents;

n is 0, 1, 2, 3 or 4;

provided that the values of m, n and $Ar^1$ are selected such that the number of contiguous atoms in the chain —$(CH_2)_m$—$Ar^1$—$(CH_2)_n$— between the two nitrogen atoms to which it is attached is in the range of from 7 to 12;

$R^5$ is selected from hydrogen, (1-6C)alkyl, $Ar^2$, —$CH_2$ $Ar^2$ and —$CH_2CH_2NHC(O)R^{5a}$; where $Ar^2$ represents phenyl, (3-6C)cycloalkyl or (3-5C)heteroaryl containing 1 or 2 heteroatoms selected from oxygen, nitrogen or sulfur, wherein the phenyl and heteroaryl groups are unsubstituted or substituted with 1 to 3 substituents selected independently from halo, (1-4C)alkyl, (1-4C)alkoxy and methylenedioxy; and wherein $R^{5a}$ represents (1-4C)alkyl;

$R^6$ is hydrogen or (1-6C)alkyl; or $R^5$ and $R^6$ together with the nitrogen atom to which they are attached form a (3-5C)azacycloalkyl group; or when $Ar^1$ represents heteroarylene, $R^5$ and $R^6$ together with the nitrogen atom to which they are attached can additionally form a morpholin-1-yl or 4-(1-6C)alkylpiperazin-1-yl group; and wherein each alkyl group in $R^1$, $R^2$, $R^3$, $R^{4a}$, $R^{4b}$, $R^5$, $R^6$ and $R^{a-c}$ is optionally substituted with from 1 to 5 fluoro substituents;

or a pharmaceutically acceptable salt or solvate or stereoisomer thereof.

2. The compound of claim 1, wherein a, b and c each represents 0.

3. The compound of claim 1, wherein $R^{4a}$ and $R^{4b}$ are hydrogen.

4. The compound of claim 1, wherein m is 2, 3 or 4.

5. The compound of claim 1, wherein n is 0, 2 or 3.

6. The compound of any one of claims 1 to 5, wherein $Ar^1$ represents 1,3-phenylene, 1,4-phenylene or 2,5-thienylene; wherein the phenylene or thienylene group is unsubstituted or substituted.

7. The compound of any one of claims 1 to 5, wherein $R^5$ is (1-4C)alkyl.

8. The compound of any one of claims 1 to 5, wherein $R^6$ is hydrogen or methyl.

9. The compound of claim 1, where a, b, and c are 0; $R^{4a}$ and $R^{4b}$ are hydrogen; $Ar^1$ is phen-1,4-ylene, unsubstituted or substituted with 1 to 4 substituents selected independently from halo, (1-4C)alkyl or (1-4C)alkoxy; wherein each alkyl and alkoxy group is optionally substituted with from 1 to 3 fluoro substituents; and m+n is an integer from 3 to 8.

10. The compound of claim 9, wherein m is 4 and n is 0, or m is 2 and n is 2, or m is 3 and n is 2.

11. The compound of claim 1, where a, b, and c are 0; $R^{4a}$ and $R^{4b}$ are hydrogen; $Ar^1$ is phen-1,3-ylene, unsubstituted or substituted with 1 to 4 substituents selected independently from halo, (1-4C)alkyl or (1-4C)alkoxy; wherein each alkyl and alkoxy group is optionally substituted with from 1 to 3 fluoro substituents; and m+n is an integer from 4 to 9.

12. The compound of claim 11, wherein m is 2 and n is 4, or m is 3 and n is 3.

13. The compound of claim 1, where a, b, and c are 0; $R^{4a}$ and $R^{4b}$ are hydrogen; $Ar^1$ is 2,5-thiophene, unsubstituted or substituted with 1 to 2 substituents selected independently from halo, (1-4C)alkyl or (1-4C)alkoxy; wherein each alkyl and alkoxy group is optionally substituted with from 1 to 3 fluoro substituents; and m+n is an integer from 4 to 9.

14. The compound of claim 13, wherein m is 3 and n is 3.

15. The compound of claim 13, wherein $R^5$ and $R^6$ together with the nitrogen atom to which they are attached form a morpholin-1-yl or 4-(1-6C)alkylpiperazin-1-yl group.

16. The compound of any one of claims 10, 12 and 14, where $R^5$ is selected from hydrogen; (1-4C)alkyl; —$CH_2Ar^2$ where $Ar^2$ represents phenyl, furan-2-yl, 3,4-methylenedioxyphenyl, or 5-methylpyrazin-2-yl; and —$CH_2CH_2NHCOR^{5a}$, where $R^{5a}$ is methyl.

17. The compound of any one of claims 9, 11 and 13, where $R^6$ is hydrogen or methyl.

18. The compound of any one of claims 9, 11 and 13, where $R^5$ and $R^6$ together with the nitrogen atom to which they are attached form a (3-4C)azacycloalkyl group.

19. A compound selected from:
2-{(S)-1-[4-(4-aminophenyl)butyl]pyrrolidin-3-yl}-2,2-diphenylacetamide;
2-((S)-1-{2-[4-(2-methylaminoethyl)phenyl]ethyl}pyrrolidin-3-yl)-2,2-diphenylacetamide;
2-((S)-1-{2-[3-(2-methylaminoethyl)phenyl]ethyl}-pyrrolidin-3-yl)-2,2-diphenylacetamide;
2-((S)-1-{3-[5-(3-methylaminopropyl)thiophen-2-yl]propyl}-pyrrolidin-3-yl)-2,2-diphenylacetamide;
2-((S)-1-{3-[3-(3-methylaminopropyl)phenyl]propyl}-pyrrolidin-3-yl)-2,2-diphenylacetamide;
2-((S)-1-{3-[4-(2-methylaminoethyl)phenyl]propyl}-pyrrolidin-3-yl)-2,2-diphenylacetamide;
2-[(S)-1-{3-[5-(3-ethylaminopropyl)thiophen-2-yl]propyl}-pyrrolidin-3-yl]-2,2-diphenylacetamide;
2-[(S)-1-{3-[5-(3-isopropylaminopropyl)thiophen-2-yl]propyl}-pyrrolidin-3-y]-2,2-diphenylacetamide;
2-[(S)-1-{3-[5-(3-dimethylaminopropyl)thiophen-2-yl]-propyl}pyrrolidin-3-yl]-2,2-diphenylacetamide;
2-[(S)-1-{2-[4-(2-ethylaminoethyl)phenyl]ethyl}pyrrolidin-3-yl]-2,2-diphenylacetamide;
2-[(S)-1-{2-[4-(2-isopropylaminoethyl)phenyl]ethyl}pyrrolidin-3-yl]-2,2-diphenylacetamide;
2-[(S)-1-{2-[4-(2-dimethylaminoethyl)phenyl]ethyl}pyrrolidin-3-yl]-2,2-diphenylacetamide;
2,2-diphenyl-2-[(S)-1-{2-[4-(2-pyrrolidin-1-ylethyl)phenyl]ethyl}pyrrolidin-3-yl]acetamide;
2-[(S)-1-(2-{4-[2-(benzylmethylamino)ethyl]phenyl}ethyl)-pyrrolidin-3-yl]-2,2-diphenylacetamide;

2-[(S)-1-(2-{4-[2-(2-acetylaminoethylamino)ethyl]
  phenyl}ethyl)pyrrolidin-3-yl]-2,2-diphenylacetamide;
2-{(S)-1-[2-(4-{2-[(5-methylpyrazin-2-ylmethyl)amino]
  ethyl}-phenyl)ethyl]pyrrolidin-3-yl}-2,2-diphenylac-
  etamide;
2-{(S)-1-[2-(4-{2-[(furan-2-ylmethyl)amino]
  ethyl}phenyl)ethyl]pyrrolidin-3-yl}-2,2-diphenylac-
  etamide;
2-{(S)-1-[2-(4-{2-[(benzo[1,3]dioxol-5-ylmethyl)amino]
  ethyl}-phenyl)ethyl]pyrrolidin-3-yl}-2,2-diphenylac-
  etamide;
2-((S)-1-{2-[4-(2-azetidin-1-ylethyl)phenyl]
  ethyl}pyrrolidin-3-yl)-2,2-diphenylacetamide,
2-[(S)-1-(3-{5-[3-(2-acetylaminoethylamino)propyl]
  thiophen-2-yl}-propyl)pyrrolidin-3-yl]-2,2-dipheny-
  lacetamide;
2-{(S)-1-[3-(5-{3-[(5-methylpyrazin-2-ylmethyl)amino]
  propyl}thiophen-2-yl)propyl]pyrrolidin-3-yl}-2,2-
  diphenylacetamide;
2-{(S)-1-[3-(5-{3-[(furan-2-ylmethyl)amino]
  propyl}thiophen-2-yl)-propyl]pyrrolidin-3-yl}-2,2-
  diphenylacetamide;
2-{(S)-1-[3-(5-{3-[(benzo[1,3]dioxol-5-ylmethyl)amino]
  propyl}thiophen-2-yl)propyl]pyrrolidin-3-yl}-2,2-
  diphenylacetamide;
2-[(S)-1-(3-{5-[3-(4-methylpiperazin-1-yl)propyl]
  thiophen-2-yl}propyl)pyrrolidin-3-yl]-2,2-diphenylac-
  etamide;
2-((S)-1-{3-[5-(3-morpholin-4-yl-propyl)thiophen-2-yl]
  propyl}pyrrolidin-3-yl)-2,2-diphenylacetamide; and
2-((S)-1-{3-[5-(3-azetidin-1-ylpropyl)thiophen-2-yl]
  propyl}pyrrolidin-3-yl)-2,2-diphenylacetamide;
or a pharmaceutically acceptable salt or solvate thereof.

20. A pharmaceutical composition comprising a pharmaceutically acceptable carrier and a therapeutically effective amount of a compound of claim 1 or 19.

21. The pharmaceutical composition of claim 20, wherein the composition further comprises a therapeutically effective amount of an agent selected from $\beta_2$ adrenergic receptor agonists, steroidal anti-inflammatory agents, phosphodiesterase-4 inhibitors, and combinations thereof.

22. The pharmaceutical composition of claim 21, wherein the composition comprises a therapeutically effective amount of a $\beta_2$ adrenergic receptor agonist and a steroidal anti-inflammatory agent.

23. A process for preparing a compound of claim 1 or 19, the process comprising:
  (a) reacting a compound of formula II:

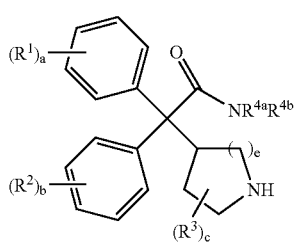

II with a compound of formula III:

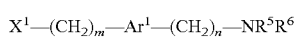

$X^1$—$(CH_2)_m$—$Ar^1$—$(CH_2)_n$—$NR^5R^6$     III wherein $X^1$ represents a leaving group;

(b) reacting a compound of formula IV:

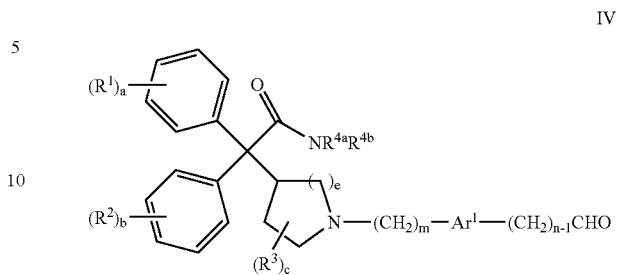

IV with a compound of formula V:

$HNR^5R^6$     V in the presence of a reducing agent;
  (c) reacting a compound of formula VI:

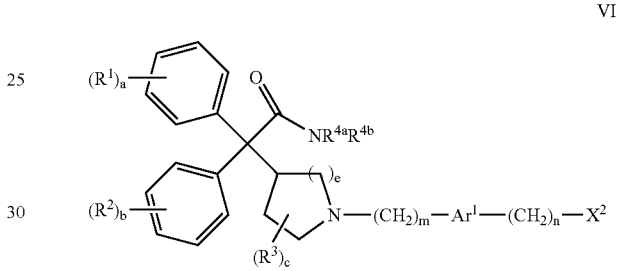

VI wherein $X^2$ represents a leaving group, with a compound of formula V;
  (d) reacting a compound of formula II with a compound of formula VII:

OHC—$(CH_2)_{m-1}$—$Ar^1$—$(CH_2)_n$—$NR^5R^6$     VII in the presence of a reducing agent; or
  (e) reacting a compound of formula VIII:

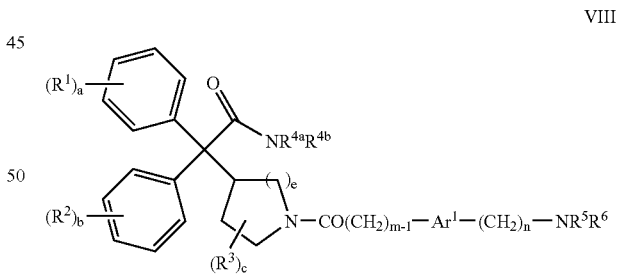

VIII with a reducing agent; to provide a compound of formula I.

24. The process of claim 23, wherein the process further comprises forming a pharmaceutically acceptable salt of the compound of formula I.

25. A method of treating chronic obstructive pulmonary disease or asthma, the method comprising administering to a patient a therapeutically effective amount of a compound of claim 1 or 19.

* * * * *

UNITED STATES PATENT AND TRADEMARK OFFICE
CERTIFICATE OF CORRECTION

| | |
|---|---|
| PATENT NO. | : 7,250,414 B2 |
| APPLICATION NO. | : 11/077391 |
| DATED | : July 31, 2007 |
| INVENTOR(S) | : Mammen et al. |

It is certified that error appears in the above-identified patent and that said Letters Patent is hereby corrected as shown below:

Column 51, line 10, "carbon" should read --nitrogen--.

Column 52, line 55, "-pyrrolidin-3-y]" should read -- -pyrrolidin-3-yl]--.

Signed and Sealed this

Fourth Day of December, 2007

JON W. DUDAS
*Director of the United States Patent and Trademark Office*